(12) United States Patent
Fukuda et al.

(10) Patent No.: US 10,591,709 B2
(45) Date of Patent: Mar. 17, 2020

(54) CELL IMAGING APPARATUS AND CELL IMAGING METHOD

(71) Applicant: SYSMEX CORPORATION, Kobe-shi, Hyogo (JP)

(72) Inventors: Masakazu Fukuda, Kobe (JP); Yanyan Liu, Kobe (JP); Toshihiro Ootani, Kobe (JP)

(73) Assignee: SYSMEX CORPORATION, Kobe-shi (JP)

(*) Notice: Subject to any disclaimer, the term of this patent is extended or adjusted under 35 U.S.C. 154(b) by 737 days.

(21) Appl. No.: 15/078,051

(22) Filed: Mar. 23, 2016

(65) Prior Publication Data

US 2016/0291306 A1    Oct. 6, 2016

(30) Foreign Application Priority Data

Mar. 31, 2015  (JP) .................. 2015-073989

(51) Int. Cl.
   *G02B 21/24*       (2006.01)
   *G01N 15/14*       (2006.01)
   (Continued)

(52) U.S. Cl.
   CPC ....... *G02B 21/241* (2013.01); *G01N 15/1434* (2013.01); *G01N 15/1475* (2013.01);
   (Continued)

(58) Field of Classification Search
   CPC .... G02B 21/241; G02B 21/244; G02B 21/26; G02B 21/36; G02B 21/365; G01N 15/1434; G01N 15/1475
   (Continued)

(56) References Cited

U.S. PATENT DOCUMENTS

2004/0189988 A1* 9/2004 Scaduto ............... G02B 21/26
                                                     356/244
2005/0006595 A1  1/2005 Goodwin et al.
                  (Continued)

FOREIGN PATENT DOCUMENTS

CN     101036043 A    9/2007
JP    2010-169484 A   8/2010
                  (Continued)

*Primary Examiner* — Sath V Perungavoor
*Assistant Examiner* — Kristin Dobbs
(74) *Attorney, Agent, or Firm* — Metrolex IP Law Group, PLLC

(57) ABSTRACT

A cell imaging apparatus captures images of cells contained in a liquid specimen comprising: an image capture unit including an objective lens, specimen cells each including an inner space which is capable of holding a liquid specimen and which is elongated in one direction, the specimen cells arranged such that the inner spaces are aligned in a row in a longitudinal direction of the inner spaces, a drive unit that moves at least one of: a) one or more specimen cells; and b) the objective lens; and a controller that controls the drive unit to move at least one of: a) one or more specimen cells; and b) the objective lens in the longitudinal direction and controls the image capture unit to capture images of cells contained in a liquid specimen held in the inner space of each of the specimen cells at multiple image capture positions.

20 Claims, 12 Drawing Sheets

(51) Int. Cl.
  *G02B 21/36* (2006.01)
  *G02B 21/26* (2006.01)
  *H04N 5/225* (2006.01)
  *H04N 5/232* (2006.01)
  *G01N 15/10* (2006.01)
  *G01N 33/493* (2006.01)
  *G01N 15/00* (2006.01)

(52) U.S. Cl.
  CPC ........... *G02B 21/244* (2013.01); *G02B 21/26* (2013.01); *G02B 21/36* (2013.01); *G02B 21/365* (2013.01); *H04N 5/2254* (2013.01); *H04N 5/232* (2013.01); *G01N 33/493* (2013.01); *G01N 2015/0065* (2013.01); *G01N 2015/1006* (2013.01); *G01N 2015/1452* (2013.01); *H04N 5/2256* (2013.01); *H04N 5/23212* (2013.01); *H04N 5/23245* (2013.01)

(58) Field of Classification Search
  USPC .......................................................... 348/80
  See application file for complete search history.

(56) References Cited

U.S. PATENT DOCUMENTS

| | | | |
|---|---|---|---|
| 2008/0123185 A1* | 5/2008 | Yoneyama | G02B 21/16 359/383 |
| 2009/0026386 A1 | 1/2009 | Goodwin et al. | |
| 2009/0028413 A1 | 1/2009 | Goodwin et al. | |
| 2010/0183216 A1* | 7/2010 | Yamada | G01N 15/1475 382/134 |
| 2011/0249109 A1* | 10/2011 | Fine | G01N 21/6408 348/79 |
| 2012/0035859 A1* | 2/2012 | Thomas | G01N 15/1429 702/19 |
| 2013/0194647 A1 | 8/2013 | Tovey | |
| 2014/0341779 A1* | 11/2014 | Takemoto | G01N 33/491 422/73 |
| 2015/0160447 A1* | 6/2015 | Okugawa | G02B 21/26 348/79 |
| 2016/0252715 A1* | 9/2016 | Nakano | G02B 27/0025 359/385 |

FOREIGN PATENT DOCUMENTS

| | | |
|---|---|---|
| WO | 00-03246 A2 | 1/2000 |
| WO | 2004-088573 A1 | 10/2004 |
| WO | 2004-113922 A2 | 12/2004 |
| WO | 2006062131 A1 | 6/2006 |
| WO | 2010-122147 A1 | 10/2010 |

* cited by examiner

CELL IMAGING APPARATUS AND CELL IMAGING METHOD

CROSS REFERENCE TO RELATED APPLICATIONS

This application claims priority based on 35 USC 119 from prior Japanese Patent Application No. 2015-073989 filed on Mar. 31, 2015, entitled "CELL IMAGING APPARATUS AND CELL IMAGING METHOD", the entire contents of which are hereby incorporated by reference.

FIELD OF THE INVENTION

The invention relates to a cell imaging apparatus and a cell imaging method which are used to capture images of cells contained in a liquid specimen.

BACKGROUND

Japanese Patent Application Publication No. 2010-169484 discloses a sample processing system including: a smear preparation apparatus that prepares a smear by dropping a blood sample onto a microscope slide; a smear imaging apparatus that captures an image of the smear prepared by the smear preparation apparatus and processes the captured image; and a smear transport apparatus that transports the microscope slide smeared with the blood from the smear preparation apparatus to the smear imaging apparatus. The smear imaging apparatus includes a microscope unit. The microscope unit includes a chuck unit. The chuck unit holds the microscope slide transported by the smear transport apparatus, and sets the microscope slide to an XY stage. Next, the microscope unit moves the XY stage in an X direction and a Y direction, and executes an operation of detecting white blood cells in the blood smeared on the microscope slide with a line sensor. Upon detection of a white blood cell, the microscope unit executes an autofocus operation of adjusting the focus of an objective lens, and captures an image of the white blood cell with a CCD camera. When the next microscope slide is transported by the smear transport apparatus to the smear imaging apparatus, the microscope unit executes another image capture operation in the same procedure.

SUMMARY

A cell imaging apparatus of this disclosure includes an image capture unit, specimen cells, a drive unit, and a controller. The image capture unit includes an objective lens. Each of the specimen cells includes an inner space which is capable of holding a liquid specimen and which is elongated in one direction. The specimen cells are arranged such that the inner spaces are aligned in a row in a longitudinal direction of the inner spaces. The drive unit moves at least one of: a) one or more specimen cells; and b) the objective lens. The controller controls the drive unit to move at least one of: a) one or more specimen cells; and b) the objective lens in the longitudinal direction, and controls the image capture unit to capture images of cells contained in a liquid specimen held in each of the inner spaces of the specimen cells at multiple image capture positions.

A cell imaging method of this disclosure uses a first specimen cell and a second specimen cell each including an inner space which is capable of holding a liquid specimen and is elongated in one direction, the first and second specimen cells arranged such that the inner spaces are aligned in a row in a longitudinal direction of the inner spaces. In this cell imaging method, a first liquid specimen containing cells is introduced into the inner space of the first specimen cell, and a second liquid specimen containing cells is introduced into the inner space of the second specimen cell. In this cell imaging method, images of the cells contained in a first liquid specimen held in the inner space of the first specimen cell are captured at multiple image capture positions by moving at least one of: a) the first and second specimen cells; and b) the objective lens in the longitudinal direction, and images of the cells contained in a second liquid specimen held in the inner space of the second specimen cell are captured at multiple image capture positions by moving at least one of: a) the first and second specimen cells; and b) the objective lens in the longitudinal direction.

In another cell imaging method of this disclosure, a first liquid specimen containing cells is introduced into a first specimen cell, and, during a period in which the cells in the first liquid specimen are allowed to settle in the first specimen cell, a second liquid specimen containing cells is introduced into a second specimen cell. In this cell imaging method, during a period in which the cells in the second liquid specimen are allowed to settle in the second specimen cell, images of the cells contained in the first liquid specimen in the first specimen cell are captured. In this cell imaging method, after completion of the capturing of the image of the cells contained in the first liquid specimen, the first liquid specimen is discharged from the first specimen cell, and a third liquid specimen containing cells is introduced into the first specimen cell. Then, during a period in which the cells in the third liquid specimen are allowed to settle in the first specimen cell, images of the cells contained in the second liquid specimen in the second specimen cell are captured.

DETAILED DESCRIPTION

Figure 1:
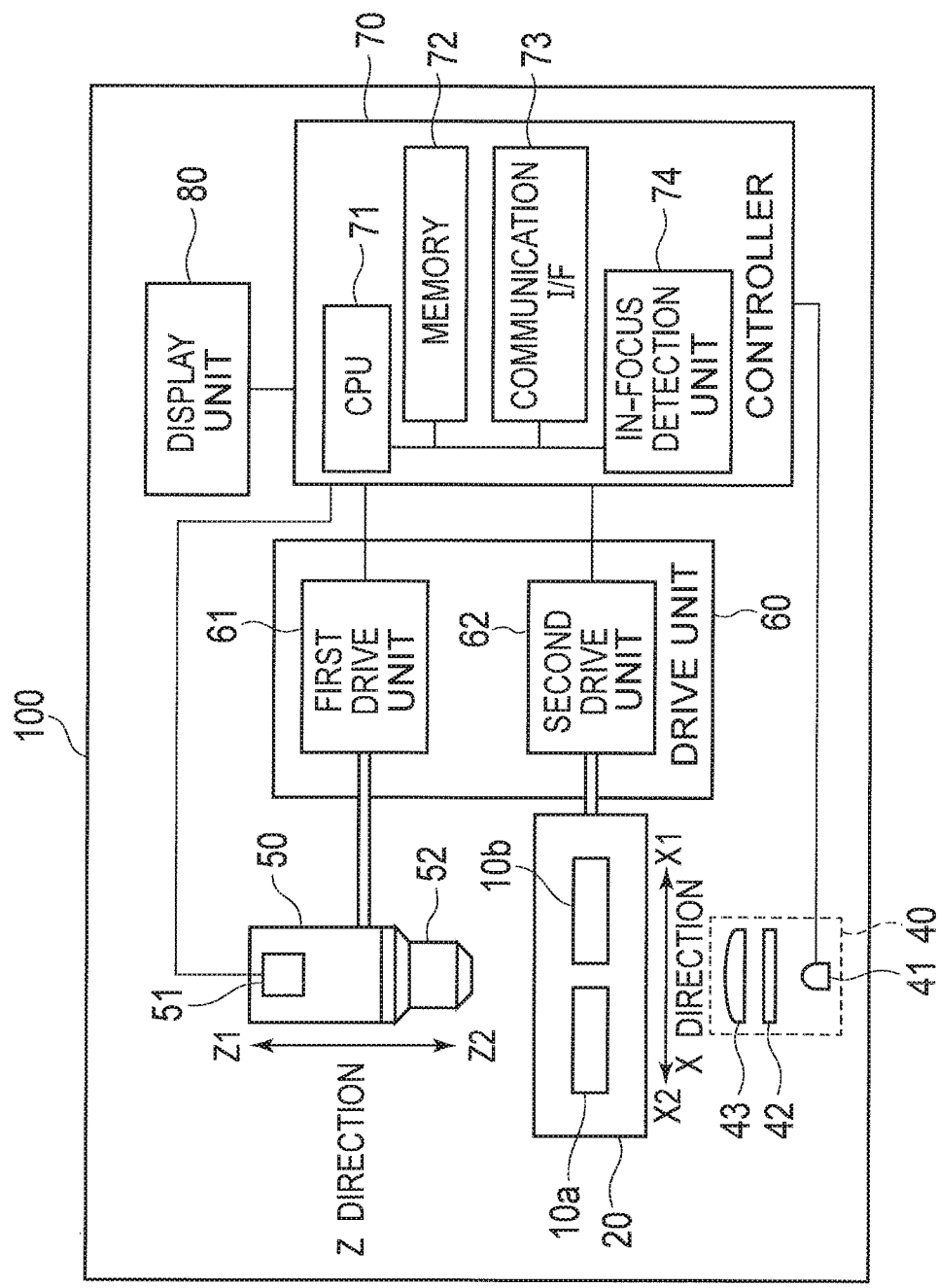
FIG. 1 is a schematic diagram illustrating a configuration of a cell imaging apparatus according to an embodiment.

Hereinafter, preferred embodiments are described with reference to the drawings.

<Configuration of Cell Imaging Apparatus>

A configuration of a cell imaging apparatus is described with reference to FIG. 1. Cell imaging apparatus 100 includes first specimen cell 10a, second specimen cell 10b, stage 20, light source unit 40, image capture unit 50, drive unit 60, controller 70, and display unit 80. Cell imaging apparatus 100 is an apparatus that captures images of cells contained in a liquid specimen, for example, cells in a urine specimen taken from a subject. Cell imaging apparatus 100 is configured to charge first specimen cell 10a with a urine specimen, charge second specimen cell 10b with a urine specimen, cause image capture unit 50 to capture images of cells in the first specimen cell 10a, and cause image capture unit 50 to capture images of cells in second specimen cell 10b. The liquid specimen subjected to the image capture may be any, as long as the liquid specimen is a biological specimen containing cells of multiple types with difference sizes. For example, the liquid specimen may be blood, coelomic fluid, uterine cervical tissue, or the like.

Image capture unit 50 includes image capture element 51, which is a CCD image sensor or a CMOS image sensor, and objective lens 52. First specimen cell 10a and second specimen cell 10b are attached to stage 20. On stage 20, first specimen cell 10a and second specimen cell 10b are aligned in an X direction, which is one of the horizontal directions. The X direction is a direction that intersects with a vertical direction. The X direction includes an X1 direction extending from first specimen cell 10a to second specimen cell 10b, and an X2 direction extending from second specimen cell 10b to first specimen cell 10a. Note that first specimen cell 10a and second specimen cell 10b may be arranged in a Y direction perpendicular to the X direction.

Three or more specimen cells may be provided on stage 20. In such a case, the three or more specimen cells are aligned in a row in the X direction on stage 20.

Figure 2:
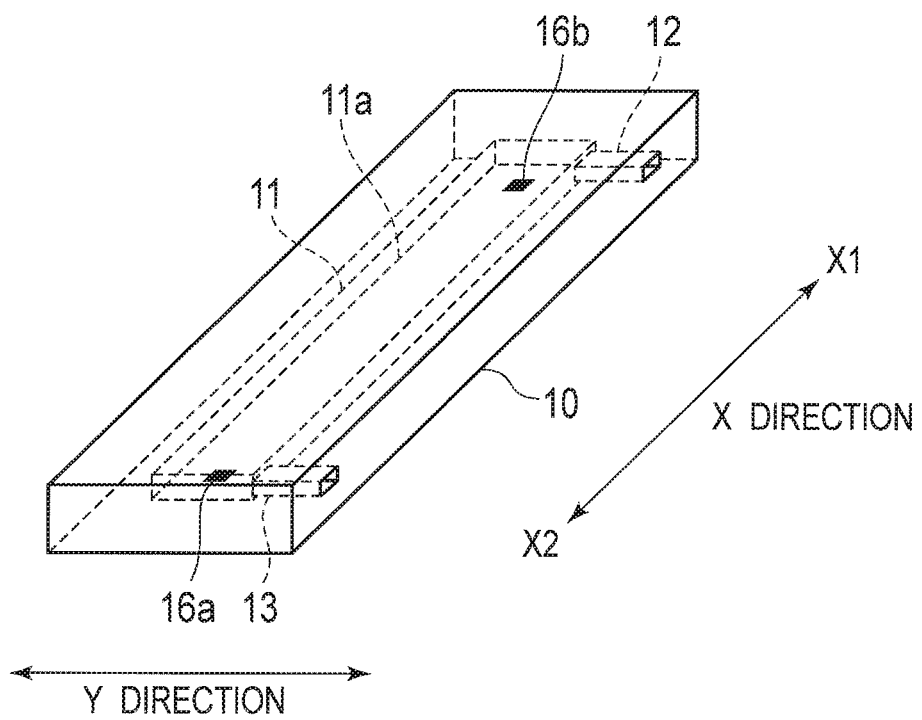
FIG. 2 is a perspective view illustrating a configuration of a specimen cell according to the embodiment.

As shown in FIG. 2, first specimen cell 10a and second specimen cell 10b have the same configuration. Here, first specimen cell 10a and second specimen cell 10b are referred to specimen cells 10. Each specimen cell 10 includes inner space 11 that holds a urine specimen, inlet port 12 communicating with inner space 11, and outlet port 13 communicating with inner space 11. Specimen cell 10 is shaped like a flat cuboid elongated in one direction and is made of a transparent material. Inner space 11 is a space having a flat cuboid shape elongated in the one direction, and is provided inside specimen cell 10. A longitudinal direction of inner space 11 is the same as a longitudinal direction of specimen cell 10, and specifically the two directions are the X direction. Each surface of inner space 11 is flat. In other words, as illustrated in FIG. 1, inner space 11 of first specimen cell 10a and inner space 11 of second specimen cell 10b are aligned in a row in the X direction, which is the longitudinal direction of inner spaces 11.

In FIG. 2, from one end of inner space 11, inlet port 12 extends in the Y direction, which is perpendicular to the longitudinal direction. From another end of inner space 11, outlet port 13 extends in the Y direction as in the case of inlet port 12. Each of inlet port 12 and outlet port 13 is opened to a side surface of specimen cell 10.

Specimen cell 10 includes first reference mark 16a at a position on an outlet port 13 side of inner space 11, and second reference mark 16b at a position on an inlet port 12 side of inner space 11. First reference mark 16a and second reference mark 16b are formed by laser processing on bottom surface 11a of inner space 11. First reference mark 16a and second reference mark 16b are aligned in the X direction.

First reference mark 16a and second reference mark 16b may be provided at positions not on bottom surface 11a of inner space 11 but on a place such as a top or bottom surface of specimen cell 10 or a top surface of inner space 11. Specimen cell 10 does not necessarily have to be provided with first reference mark 16a or second reference mark 16b.

Figure 3:
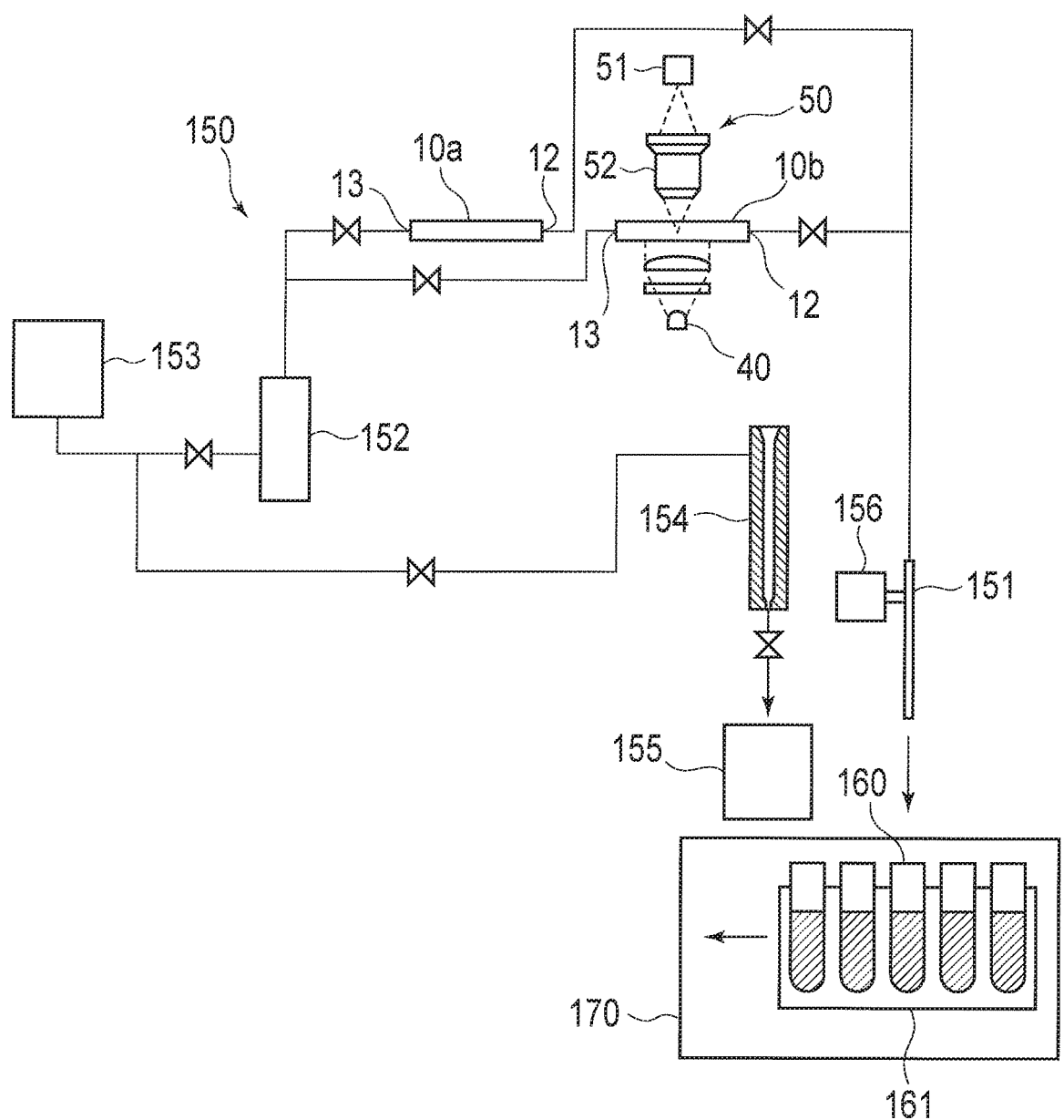
FIG. 3 is a schematic diagram illustrating a fluid circuit of an imaging unit.

As shown in FIG. 3, cell imaging apparatus 100 includes specimen introduction unit 150, aspiration tube 151, and transport unit 170. Specimen introduction unit 150 includes a tube connected to first specimen cell 10a and second specimen cell 10b, electromagnetic valves, and pump 152. A portion of the tube extending from aspiration tube 151 is branched at a certain midpoint. One of the branches is connected to inlet port 12 of first specimen cell 10a through an electromagnetic valve, and another branch is connected to inlet port 12 of second specimen cell 10b thorough another electromagnetic valve. A branch of the tube extending from outlet port 13 of first specimen cell 10a and another branch of the tube extending from outlet port 13 of second specimen cell 10b are met and connected to pump 152. An electromagnetic valve is provided between outlet port 13 of first specimen cell 10a and the meeting point, and another electromagnetic valve is provided also between outlet port 13 of second specimen cell 10b and the meeting point. Pump 152 is connected through the tube and still another electromagnetic valve to a container 153 in which a buffer is accommodated. The buffer is charged into the tube for introduction of urine specimens. Container 153 is connected to cleaning bath 154 through the tube and another electromagnetic valve. The buffer is supplied to cleaning bath 154, and used also as a cleaning solution. Waste liquid container 155 is provided below cleaning bath 154.

Aspiration tube 151 is connected to drive unit 156 including a motor. Drive unit 156 moves aspiration tube 151.

For example, transport unit 170 includes a belt conveyer, and transports rack 161 capable of holding specimen containers 160, which are urine collection tubes. When transport unit 170 transports rack 161, specimen containers 160 are transported one after another to an aspiration position below aspiration tube 151.

When first specimen cell 10a is charged with a urine specimen, and images of cells in the urine specimen are captured, the electromagnetic valve on the branch of the tube connected to first specimen cell 10a is opened, whereas the electromagnetic valve on the branch of the tube connected to second specimen cell 10b is closed. Transport unit 170 transports one of specimen containers 160 containing the urine specimen to be subjected to the image capture to the aspiration position. Aspiration tube 151 is inserted into specimen container 160. When pump 152 is operated, the urine specimen in specimen container 160 is aspirated through aspiration tube 151. After a predetermined amount of the urine specimen is aspirated, aspiration tube 151 is taken out of specimen container 160. Since pump 152 keeps operating also after aspiration tube 151 is taken out of specimen container 160, air is aspirated through aspiration tube 151, and the urine specimen is introduced through inlet port 12 to inner space 11 of first specimen cell 10a. Since the electromagnetic valves provided upstream and downstream of second specimen cell 10b are closed, no urine specimen is introduced into inner space 11 of second specimen cell 10b. Since pump 152 keeps operating until the urine specimen starts to flow out of outlet port 13 of first specimen cell 10a, the urine specimen is charged into the entire inner space 11 of first specimen cell 10a.

After images of cells contained in the urine specimen in first specimen cell 10a are captured, aspiration tube 151 and specimen cell 10a are cleaned. For the cleaning, aspiration tube 151 is moved to cleaning bath 154. When pump 152 is operated, the buffer is supplied to inner space 11 of first specimen cell 10a, and inner space 11 is cleaned. The urine specimen pushed out of inner space 11 is discharged through aspiration tube 151 to cleaning bath 154. When pump 152 is further operated, the buffer is discharged from aspiration tube 151, and the inside of aspiration tube 151 is cleaned. The buffer is supplied from container 153 to cleaning bath 154, and the outside of aspiration tube 151 is cleaned. The waste liquid from cleaning bath 154 is stored in waste liquid container 155.

When second specimen cell 10b is charged with a urine specimen, and images of cells in the urine specimen are captured, the electromagnetic valves on the branch of the tube connected to first specimen cell 10a are closed, whereas the electromagnetic valves on the branch of the tube connected to second specimen cell 10b are opened. The other operations are the same as in the case where first specimen cell 10a is charged with a urine specimen, and images of cells in the urine specimen are captured.

As shown in FIG. 2, specimen cell 10 is fixed to stage 20 with bottom surface 11a of inner space 11 on which first reference mark 16a and second reference mark 16b is provided being located on a lower side. Bottom surface 11a of specimen cell 10 extends substantially horizontally.

Specimen cell 10 is fixed to stage 20 in an undetachable manner. Specimen cell 10 may be discarded after a single use. In such a case, stage 20 is configured to allow specimen cell 10 to be attached and detached.

As shown in FIG. 1, drive unit 60 includes first drive unit 61 and second drive unit 62, and shifts the position of objective lens 52 with respect to first specimen cell 10a and second specimen cell 10b. First drive unit 61 includes an electric motor. First drive unit 61 moves image capture unit 50 in a Z direction, which is the vertical direction. The Z direction includes a Z1 direction, which is an upward vertical direction, and a Z2 direction, which is a downward vertical direction. The Z direction is an optical axis direction of objective lens 52. A focus of objective lens 52 is adjusted by moving image capture unit 50 in the Z direction.

Figure 4:
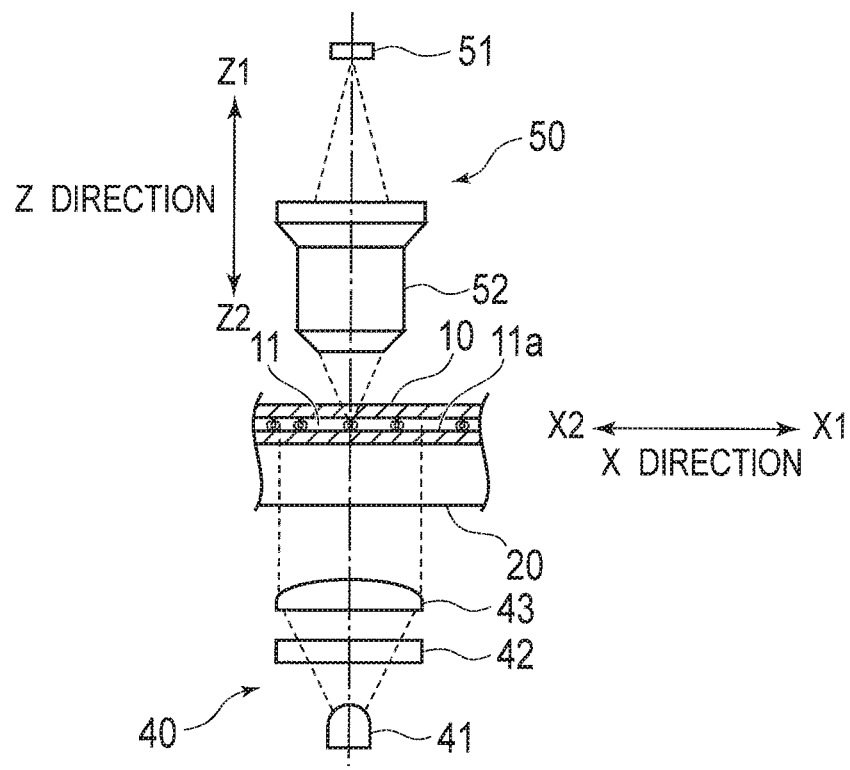
FIG. 4 is a front view illustrating a configuration of a light source unit and an image capture unit.

As shown in FIG. 4, light source unit 40 is provided below stage 20. Light source unit 40 includes LED light source 41, scattering plate 42, and lens 43. Light source 41 is a pulsed light source that emits pulsed light at regular intervals, and each emission period is 140 to 200 μsec. For irradiation of specimen cell 10 with light, light source 41 emits light upward. Scattering plate 42 and lens 43 are arranged above light source 41. Light emitted from light source 41 is scattered by scattering plate 42, and converted to parallel light by lens 43. Specimen cell 10 is irradiated with the parallel light.

Image capture unit 50 is provided above stage 20. Image capture element 51 and objective lens 52 are arranged along the same optical axis as that of light source unit 40, with image capture element 51 being located on an upper side and objective lens 52 being located on a lower side. Image capture element 51 and objective lens 52 are held in a single optical column. In other words, the distance between image capture element 51 and objective lens 52 does not change. Note that a configuration may be employed in which image capture element 51 is fixed to an optical base, and only objective lens 52 is movable. The magnification of objective lens 52 is 15 times. However, the magnification is not limited to 15 times, as long as images of cells such as white blood cells, red blood cells, and epithelial cells, and other formed elements such as urinary cast in urine can be magnified to suitable sizes.

Figure 5:
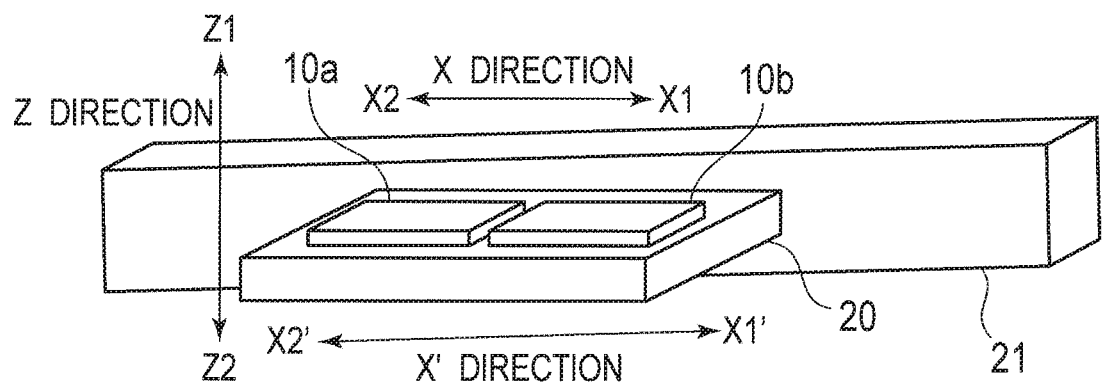
FIG. 5 is a perspective view illustrating a configuration of a mechanism for moving a stage.

As shown in FIG. 5, stage 20 is attached to linear motion guide 21. Linear motion guide 21 guides the movement of stage 20 in an X' direction, which is an inclined direction inclined from the X direction in the Z direction by a predetermined angle. An inclined angle of the X' direction from the X direction is very small, and the X' direction is substantially the same as the X direction. The X' direction includes an X1' direction, which is the X1 direction inclined in the Z direction, and an X2' direction, which is an X2 direction inclined in the Z direction. Linear motion guide 21 is a restriction unit that restricts the moving direction of stage 20 to the X' direction. First specimen cell 10a and second specimen cell 10b are fixed to stage 20. When stage 20 moves, first specimen cell 10a and second specimen cell 10b also move together with stage 20. In addition, even when stage 20 moves, the relative positional relationship between first specimen cell 10a and second specimen cell 10b does not change.

As shown in FIG. 1, second drive unit 62 includes an electric motor. Second drive unit 62 moves stage 20 in the X1' direction and the X2' direction. When stage 20 moves in the X1' direction or the X2' direction, the visual field of objective lens 52 moves in the X2 direction or the X1 direction. When the subject of the image capture is switched between first specimen cell 10a and second specimen cell 10b, second drive unit 62 moves stage 20 in the X1' direction or the X2' direction. Also in this case, the visual field of objective lens 52 moves in the X2 direction or the X1 direction.

It is also possible to employ a configuration in which drive unit 60 moves only one of image capture unit 50 and stage 20.

Even when specimen cell 10 is disposed on stage 20 so as not to be inclined from a horizontal direction, specimen cell 10 may be slightly inclined from the horizontal direction because of machine difference. Moreover, specimen cell 10 may be inclined upward from the horizontal direction or downward from the horizontal direction. In this respect, specimen cell 10 is moved in the direction inclined from the horizontal direction by a predetermined angle, which is larger than an inclination angle possibly caused by the machine difference in this embodiment. This enables the direction in which objective lens 52 is moved in an image capture step described later to be common among urine specimens, making it possible to simplify the motion mechanism and the motion control of objective lens 52.

Controller 70 includes CPU 71, memory 72, and communication interface 73. Controller 70 controls each of light source unit 40, image capture unit 50, first drive unit 61, second drive unit 62, and display unit 80. Controller 70 receives images captured by image capture unit 50. Controller 70 conducts predetermined processes on the captured images. Controller 70 includes in-focus detection unit 74 that executes an autofocus operation of image capture unit 50.

It is also possible to employ a configuration in which a personal computer executes the image processing. In this case, controller 70 communicates with the personal computer, and transmits the images of the cells to the personal computer. The personal computer performs image processing such as cutting-out of a partial image of each cell.

Display unit 80 includes a liquid-crystal display panel. Display unit 80 is connected to controller 70, and controlled by controller 70 to display a screen. Display unit 80 displays captured images, partial images obtained by the image processing, and the like. When a personal computer executes the image processing, the captured images or the partial images obtained by the image processing may be displayed on a display unit of the personal computer.

<Operation of Cell Imaging Apparatus>

In cell imaging apparatus 100, image capture unit 50 captures images of cells contained in urine specimens charged in inner spaces 11 of first specimen cell 10a and second specimen cell 10b. When images of cells in one specimen cell 10 are captured, the visual field of objective lens 52 is moved in the X1 direction by moving stage 20 in the X2' direction at a constant speed and simultaneously moving objective lens 52 in the Z2 direction at a constant speed, which is a moving speed according to the inclination of the X2' direction from the X2 direction. Thus, the images are captured at multiple image capture positions. In this manner, the focus can be adjusted to the vicinity of the bottom surface of inner space 11, without detecting an in-focus state at each image capture position. When the subject of the image capture is switched between first specimen cell 10a and second specimen cell 10b, stage 20 is moved in the X1' direction or the X2' direction. The operations of cell imaging apparatus 100 are described below.

Figure 6:
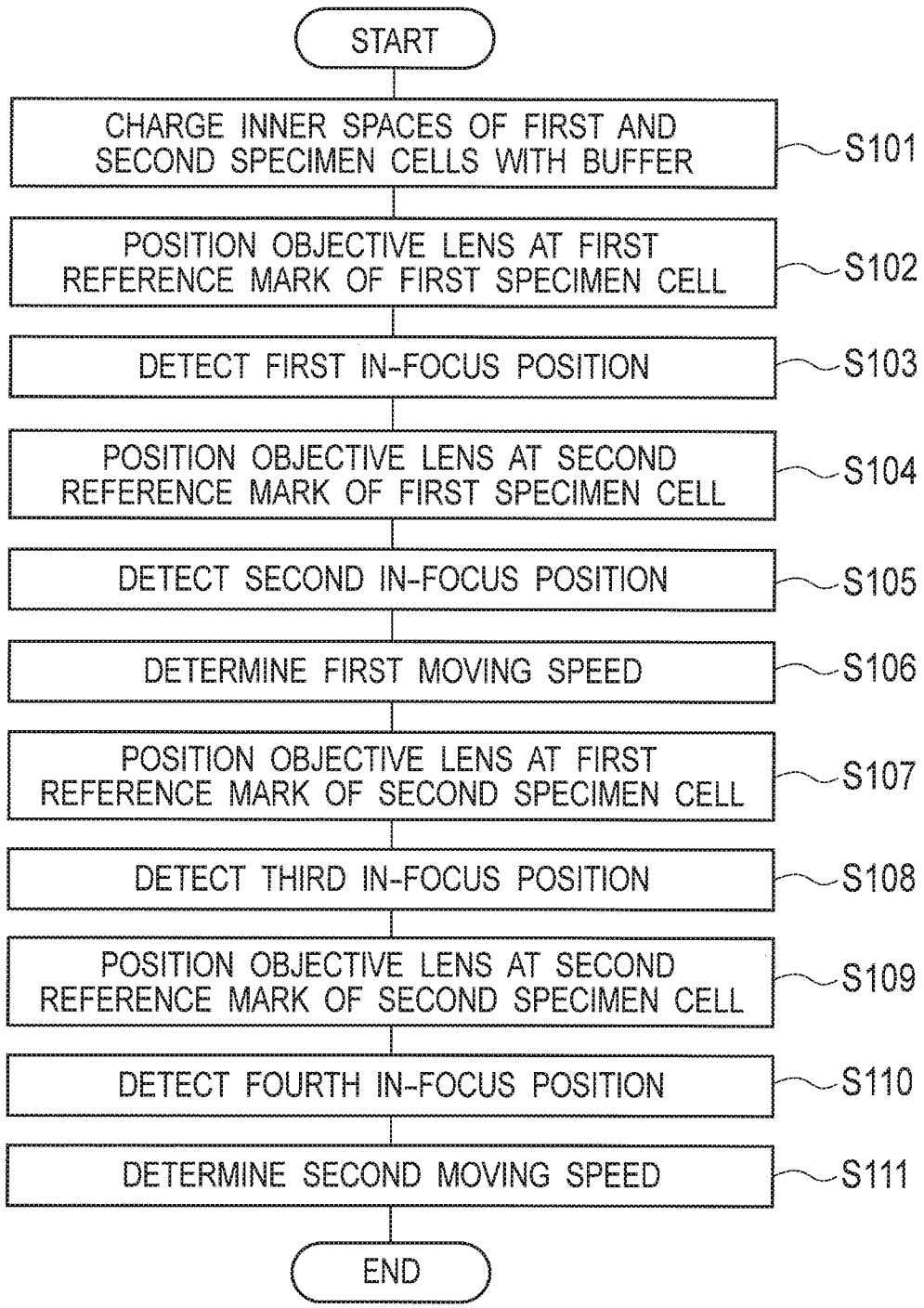
FIG. 6 is a flowchart illustrating a procedure of a moving speed determination operation.

When a user activates cell imaging apparatus 100, cell imaging apparatus 100 executes an initialization operation. The initialization operation includes a moving speed determination operation of determining the moving speed of image capture unit 50 in capturing images of cells in urine. With reference to FIG. 6, the moving speed determination operation is described.

In Step S101, CPU 71 controls pump 152 to charge the buffer into flow paths extending from container 153 thorough first specimen cell 10a or second specimen cell 10b to aspiration tube 151. Consequently, the buffer is held in inner spaces 11 of first specimen cell 10a and second specimen cell 10b.

In Step S102, CPU 71 controls second drive unit 62 to move stage 20 in the X2' direction and position image capture unit 50 at first reference mark 16a on the outlet port 13 side of first specimen cell 10a.

In Step S103, CPU 71 detects a first in-focus position, which is an in-focus position of objective lens 52 at first reference mark 16a of first specimen cell 10a. To detect the first in-focus position, controller 70 executes an autofocus operation three times. In each autofocus operation, first drive unit 61 moves objective lens 52 in the Z1 direction or the Z2 direction, and in-focus detection unit 74 detects a state where first reference mark 16a comes into focus.

The autofocus operation is based on a contrast detection method. The position of objective lens 52 at which the contrast of an image acquired by image capture element 51 can be maximized is detected as an in-focus position of objective lens 52. The detected in-focus position is stored in memory 72 of controller 70.

An autofocus operation based on a method other than the contrast detection method may be employed. For example, it is possible to employ known autofocus operations such as those based on the phase-difference detection method, the line sensor method, the ultrasonic method, the infrared method, and the like.

CPU 71 excludes one of the obtained three in-focus positions which has the most distant numeric value indicating the in-focus position, and determines an average value of the remaining two in-focus positions. CPU 71 stores the obtained average value as the first in-focus position in memory 72.

In Step S104, CPU 71 controls second drive unit 62 to move stage 20 in the X2' direction, and positions image capture unit 50 at second reference mark 16b on the inlet port 12 side of first specimen cell 10a. Since first reference mark 16a and second reference mark 16b are aligned in the X2 direction, a state where objective lens 52 faces first reference mark 16a can be shifted to a state where objective lens 52 faces second reference mark 16b only by moving stage 20 in the X2' direction.

In Step S105, CPU 71 detects a second in-focus position, which is an in-focus position of objective lens 52 at second reference mark 16b of first specimen cell 10a. To detect the second in-focus position, controller 70 executes an autofocus operation three times.

CPU 71 excludes one of the three obtained in-focus positions which has the most distant numeric value indicating the in-focus position, and determines an average value of the remaining two in-focus positions. CPU 71 stores the obtained average value as the second in-focus position in memory 72.

The first and second in-focus positions may be detected by using two positions in first specimen cell 10a where no reference marks are provided. The first and second in-focus positions may be detected not in the state where inner space 11 is charged with the buffer but in a state where inner space 11 is charged with a urine specimen, or in a state where inner space 11 is filled with air. It is also possible to detect the first and second in-focus positions by charging inner space 11 with a control specimen containing standard particles having a predetermined size, and adjusting the focus on the standard particles. The same shall apply to second specimen cell 10b.

The number of times of the autofocus operation for detecting each of the first and second in-focus positions is not limited to three. The autofocus operation may be conducted only once or multiple times other than three times. Note, however, that since the increase in the number of times of the autofocus operation leads to a longer operation time, the number of times is preferably a smallest possible number. From the viewpoint of detection precision, the autofocus operation is preferably executed multiple times.

The average value of the two in-focus positions is calculated for the detection of the first in-focus position. However, the first in-focus position is not limited thereto. The first in-focus position may be an average value of three in-focus positions, or may be the central one of the three in-focus positions. The same shall apply to the second in-focus position.

In Step S106, CPU 71 determines a first moving speed, which is a moving speed of objective lens 52 for first specimen cell 10a, by using the first in-focus position and the second in-focus position.

Figure 7:
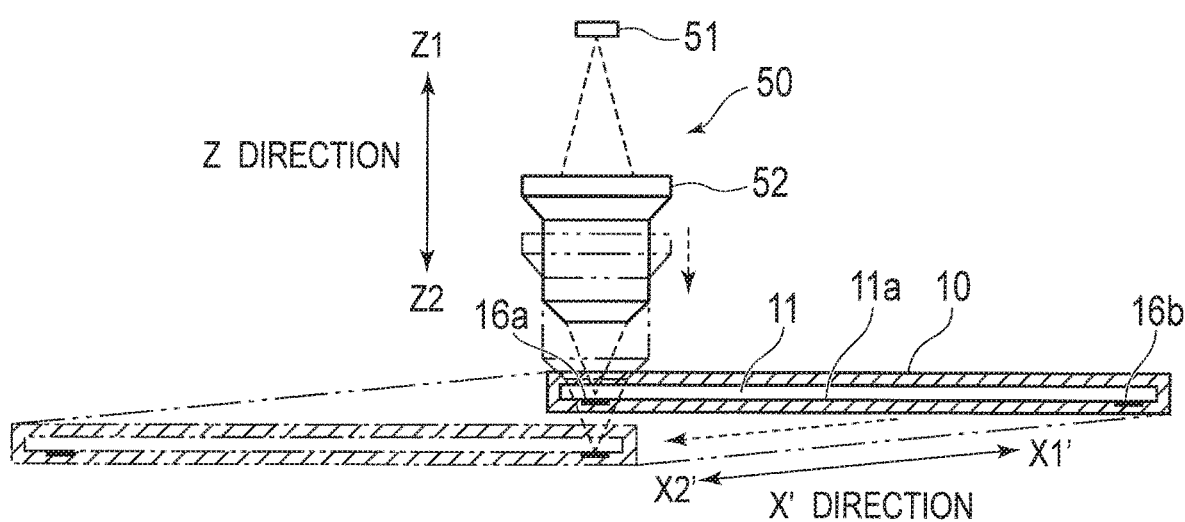
FIG. 7 is a diagram for illustrating determination of a moving speed of an objective lens.

With reference to FIG. 7, the determination of the moving speed of objective lens 52 is described.

In one specimen cell 10, images are captured at multiple image capture positions. In the image capture step, image capture unit 50 executes image capture multiple times, while second drive unit 62 is moving stage 20 in the X2' direction at a constant speed, as described later. Since cells in the urine specimen introduced in inner space 11 are located above bottom surface 11a, cell imaging apparatus 100 adjusts the focus of objective lens 52 to a position away from bottom surface 11a by a constant distance in the upward direction for each image capture position.

As illustrated in FIG. 7, the moving direction of stage 20 is inclined from the horizontal direction. In this case, when images are captured at multiple image capture positions in specimen cell 10, the position of objective lens 52 at which the position away from bottom surface 11a of inner space 11 by the constant distance in the upward direction comes into focus is different at different image capture positions. For this reason, when stage 20 is moved in the X2' direction, while objective lens 52 is stood still, the distance between objective lens 52 and the bottom surface 11a of specimen cell 10 changes. Hence, even when the position away from bottom surface 11a by the constant distance in the upward direction is in focus at one image capture position, the position away from bottom surface 11a by the constant distance in the upward direction may be out of focus at another image capture position. To make the position away from bottom surface 11a by the constant distance in the upward direction in focus at any image capture position, it is necessary to keep constant the distance between objective lens 52 and bottom surface 11a during a period in which specimen cell 10 is moved in the X2' direction. In other words, objective lens 52 has to move in the Z direction by the same distance as a distance by which the position of specimen cell 10a is shifted in the Z direction as a results of the movement of specimen cell 10 in the X2' direction.

To keep objective lens 52 focused on the position away from bottom surface 11a by the constant distance in the upward direction, first drive unit 61 moves image capture unit 50 in the Z2 direction at a constant speed. Here, the movement of stage 20 in the X2' direction and the movement of image capture unit 50 in the Z2 direction are combined, and the resultant relative movement between specimen cell 10 and objective lens 52 is a constant-speed movement in the X direction, i.e., in the horizontal direction. Consequently, the visual field of objective lens 52 moves in the X1 direction. In Step S106, the first moving speed is determined at which objective lens 52 is to be moved in the Z2 direction during a period for which stage 20 moves in the X2' direction at the constant speed.

By moving stage 20 in the X2' direction, cells in each specimen cell are moved in the Z2 direction. Hence, the direction in which objective lens 52 is moved can be always the Z2 direction in capturing images of cells in every specimen cell. For this reason, even when the specimen cell is inclined because of machine difference, the position of objective lens 52 with respect to the specimen cell can be moved in the X direction, while the structure of drive unit 60 and the motion control of objective lens 52 are simplified.

The inclination of the X' direction from the X direction is very small, and the X' direction is substantially the same as the horizontal direction. Accordingly, the distance by which image capture unit 50 moves in the Z2 direction is much smaller than the distance by which stage 20 moves in the X2' direction. The above-described very small inclination of the X' direction from the X direction eliminates the need for a large space for moving image capture unit 50 in the Z direction, and makes it possible to prevent the increase in size of the apparatus.

Note that it is also possible to employ a configuration in which stage 20 moves not in the X' direction but in the X direction, which is the horizontal direction. In this case, image capture unit 50 does not necessarily have to be moved in the Z direction in the image capture step. It is also possible to employ a configuration in which first specimen cell 10a and second specimen cell 10b are fixed to stage 20, while being inclined from the horizontal direction so that the longitudinal directions of inner spaces 11 can be equal to the X' direction, and stage 20 is moved in the X direction. In this case, bottom surface 11a of each inner space 11 is inclined from the horizontal direction. Hence, in the image capture step, objective lens 52 is moved in the Z direction according to the amount of the movement of stage 20 to keep constant the distance between objective lens 52 and bottom surface 11a.

A period from the start to the end of the visual field movement, i.e., the period for which first drive unit 61 moves objective lens 52 (hereinafter, referred to as "set period") is set in advance. The set period is also a period for which second drive unit 62 moves stage 20. The moving speed of objective lens 52 is a speed at which objective lens 52 moves from the first in-focus position to the second in-focus position in the set period. Specifically, the moving speed of objective lens 52 is determined by calculating the distance between the first in-focus position and the second in-focus position in the Z direction, and dividing the calculated distance by the set period.

When specimen cell 10 is provided with three or more reference marks which are away from each other in the X direction, it is possible to detect an in-focus position for each of these reference marks and determine the moving speed based on the detected three or more positions.

After determining the first moving speed, CPU 71 stores first speed information indicating the first moving speed in memory 72. The first speed information is information used to adjust the focus of each visual field of the objective lens 52 in first specimen cell 10a.

See again FIG. 6. By the processes in Steps S101 to S106 described above, CPU 71 determines the first moving speed of objective lens 52 to be employed when images of cells in a urine specimen held in first specimen cell 10a are captured, as described above.

Next, by processes in Steps S107 to S111, CPU 71 determines a second moving speed, which is a moving speed of objective lens 52 for capturing images of cells in a urine specimen held in second specimen cell 10b.

In Step S107, CPU 71 controls second drive unit 62 to move stage 20 in the X2' direction and position image capture unit 50 at first reference mark 16a on the outlet port 13 side of second specimen cell 10b. Since first specimen cell 10a and second specimen cell 10b are aligned in the X2 direction, the state where objective lens 52 faces second reference mark 16b of first specimen cell 10a can be shifted to a state where objective lens 52 faces first reference mark 16a of second specimen cell 10b only by moving stage 20 in the X2' direction.

In Step S108, CPU 71 detects a third in-focus position, which is an in-focus position of objective lens 52 at first reference mark 16a of second specimen cell 10b. The process in Step S108 is the same as that in Step S103.

In Step S109, CPU 71 controls second drive unit 62 to move stage 20 in the X2' direction and position image capture unit 50 at second reference mark 16b on the inlet port 12 side of second specimen cell 10b.

In Step S110, CPU 71 detects a fourth in-focus position, which is an in-focus position of objective lens 52 at second reference mark 16b of second specimen cell 10b. The process in Step S110 is the same as that in Step S105.

In Step S111, CPU 71 determines the second moving speed by using the third in-focus position and the fourth in-focus position. The process in Step S111 is the same as that in Step S106.

After determining the second moving speed, CPU 71 stores second speed information indicating the second moving speed in memory 72. The second speed information is information used to adjust the focus of each visual field of objective lens 52 in second specimen cell 10*b*.

Since the moving speed of objective lens 52 is determined for each of first specimen cell 10*a* and second specimen cell 10*b* individually, the in-focus state can be kept even when first specimen cell 10*a* and/or second specimen cell 10*b* are inclined because of the machine difference. After Step S111, CPU 71 terminates the moving speed determination operation.

When the initialization operation is completed, cell imaging apparatus 100 is placed in a standby state. In the standby state, cell imaging apparatus 100*a* can accept a urine specimen.

In the standby state, CPU 71 can set a normal mode, which is a first mode, or a thorough examination mode, which is a second mode, selectively.

When cell imaging apparatus 100 in the standby state receives from a user an instruction to start the image capture of a urine specimen, cell imaging apparatus 100 executes a urine specimen image capture process. Hereinafter, the urine specimen image capture process is described with reference to FIGS. 8A to 8C.

At a time point where the urine specimen image capture process is started, flow paths extending from aspiration tube 151 to pump 152 including inner spaces 11 of first specimen cell 10*a* and second specimen cell 10*b* are charged with the buffer.

In Step S201, CPU 71 controls second drive unit 62 to move stage 20 in the X1' direction and position image capture unit 50 at first reference mark 16*a* on the outlet port 13 side of first specimen cell 10*a*. A moving speed of stage 20 in Step S201 is a second speed higher than the first speed, at which stage 20 moves for moving the visual field to capture images of cells.

In Step S202, CPU 71 detects the first in-focus position, which is the in-focus position of objective lens 52 at first reference mark 16*a* of first specimen cell 10*a*, and stores the first in-focus position in memory 72. Hereinafter, Step S202 is referred to as "autofocus step."

Although the first in-focus position is detected in the moving speed determination operation, the first in-focus position is detected again in the autofocus step. This is intended to correct the shift of the in-focus position with the lapse of time. The temperature of a room in which cell imaging apparatus 100 is placed may change with the lapse of time, and the change in temperature may cause changes in distances between units in cell imaging apparatus 100, for example, a change in distance between objective lens 52 and first specimen cell 10*a*. Accordingly, if objective lens 52 is positioned at the first in-focus position detected in the moving speed determination operation, the focus of objective lens 52 may be shifted from bottom surface 11*a* because of the change in temperature. For this reason, the first in-focus position is detected again in the autofocus step, and objective lens 52 is focused on bottom surface 11*a* of inner space 11.

In Step S203, CPU 71 controls transport unit 170 to position specimen container 160 containing a urine specimen to be subjected to the image capture to the aspiration position.

In Step S204, CPU 71 determines whether the urine specimen to be subjected to the image capture should be subjected to the image capture in the normal mode or in the thorough examination mode. Whether the urine specimen should be subjected to the image capture in the normal mode or in the thorough examination mode can be determined by various methods. For example, a barcode containing information indicating whether the urine specimen should be subjected to the image capture in the normal mode or in the thorough examination mode is attached to the specimen container, and the information is read out of the barcode with a barcode reader. In this manner, whether the urine specimen should be subjected to the image capture in the normal mode or in the thorough examination mode can be determined. Alternatively, a barcode of sample ID is attached to the specimen container, and the sample ID is read out with a barcode reader. Then, the sample ID is transmitted to a host computer to inquire whether the urine specimen should be subjected to the image capture in the normal mode or in the thorough examination mode. In addition, a user can designate whether the urine specimen should be subjected to the image capture in the normal mode or in the thorough examination mode by operating an input unit provided in cell imaging apparatus 100.

When the urine specimen should be subjected to the image capture in the normal mode, CPU 71 proceeds to "normal mode" in Step S204, and executes Step S205. When the urine specimen should be subjected to image capture in the thorough examination mode, CPU 71 proceeds to "thorough examination mode" in Step S204, and executes Step S233.

In Step S205, CPU 71 controls drive unit 156 and specimen introduction unit 150 to insert aspiration tube 151 into specimen container 160, aspirate a predetermined amount of the urine specimen from specimen container 160, and introduce the urine specimen into inner space 11 of first specimen cell 10*a*. The urine specimen is neither mixed with any reagent such as a staining solution or a diluent, nor subjected to centrifugation. Hereinafter, Step S205 is referred to as "specimen introduction step."

In the normal mode, the urine specimen is aspirated once per specimen container 160 in the specimen introduction step. In other words, first specimen cell 10*a* and second specimen cell 10*b* are charged with different urine specimens taken from different subjects.

In Step S206, CPU 71 waits for a predetermined period, for example, for 100 seconds. As a result, cells in the urine specimen held in first specimen cell 10*a* are settled, and many cells are disposed on bottom surface 11*a* of inner space 11. Hereinafter, Step S206 is referred to as "settlement step."

In Step S207, during the settlement step on first specimen cell 10*a*, CPU 71 controls second drive unit 62 to move stage 20 in the X2' direction and position image capture unit 50 at first reference mark 16*a* of second specimen cell 10*b*. The moving speed of stage 20 in Step S207 is the second speed as in the case of Step S201.

In Step S208, the autofocus step is executed on second specimen cell 10*b*. In other words, CPU 71 detects the third in-focus position, which is the in-focus position of objective lens 52 at first reference mark 16*a* of second specimen cell 10*b*. The process in Step S208 is the same as that in Step S202.

In Step S209, CPU 71 controls transport unit 170 to transport rack 161, and position specimen container 160 containing a next urine specimen to be subjected to the image capture at the aspiration position.

In Step S210, CPU 71 determines whether the urine specimen to be subjected to the image capture should be subjected to the image capture in the normal mode or in the thorough examination mode. The process in Step S210 is the same as that in Step S204.

When the urine specimen should be subjected to the image capture in the normal mode, CPU 71 proceeds to "normal mode" in Step S210, and executes Step S211. When the urine specimen should be subjected to image capture in the thorough examination vmode, CPU 71 proceeds to "thorough examination mode" in Step S210, and executes Step S257.

In Step S211, CPU 71 executes the specimen introduction step on second specimen cell 10*b*. In other words, CPU 71 controls drive unit 156 and specimen introduction unit 150 to insert aspiration tube 151 into specimen container 160, aspirate a predetermined amount of the urine specimen from specimen container 160, and introduce the urine specimen into inner space 11 of second specimen cell 10*b*.

In Step S212, CPU 71 starts the settlement step on second specimen cell 10*b*. In other words, CPU 71 waits for a predetermined period, for example, for 100 seconds.

In Step S213, during the settlement step on second specimen cell 10*b*, CPU 71 controls second drive unit 62 to move stage 20 in the X1' direction, and position image capture unit 50 at first reference mark 16*a* of first specimen cell 10*a*. The moving speed of stage 20 in Step S213 is the second speed as in the case of Step S201.

In Step S214, CPU 71 controls first drive unit 61 to position objective lens 52 at an image capture start position, which is a corrected position away from the first in-focus position by a predetermined offset amount in the upward direction.

Figure 9:
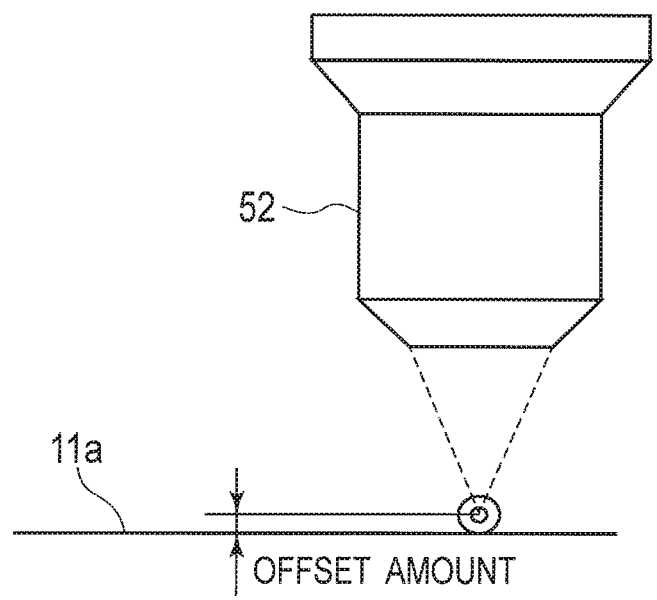
FIG. 9 is a diagram for illustrating an offset amount of the objective lens.

With reference to FIG. 9, the offset amount is described. When objective lens 52 is at the first in-focus position, objective lens 52 is focused on bottom surface 11*a*. Since most cells are arranged on bottom surface 11*a*, the focus of objective lens 52 is not on the cell. When an image is captured in this state, the image of the cell is unclear. Accordingly, to adjust the focus of objective lens 52 to the cell, objective lens 52 is moved upward by an amount which is about equal to the radius of the cell, and the focus of objective lens 52 is positioned near a center of the cell.

The offset amount is stored in memory 72 in advance. When the offset amount is set to, for example, 5 to 6 μm, objective lens 52 is focused on red blood cells. Note, however, that the offset amount does not necessarily have to be 5 to 6 μm, but the offset amount can be set, as appropriate, according to the sizes of cells of interest.

When first reference mark 16*a* and second reference mark 16*b* are provided in a place other than bottom surface 11*a* of inner space 11 of specimen cell 10, the offset amount may be a distance from the surface on which first reference mark 16*a* and second reference mark 16*b* are provided to the position of the center of the cell of interest in the Z direction.

In Step S215 of FIG. 8, CPU 71 reads out the first speed information for first specimen cell 10*a* from memory 72.

After completion of the settlement step on first specimen cell 10*a*, CPU 71 executes in Step S216 the image capture step in which images of cells are captured in multiple visual fields. In the image capture step, CPU 71 controls first drive unit 61 and second drive unit 62 to simultaneously start the movement of stage 20 in the X2' direction and the movement of image capture unit 50 in the Z2 direction. First drive unit 61 moves image capture unit 50 in the Z2 direction for the set period at the first moving speed indicated in the first speed information without any stop during the movement. Meanwhile, second drive unit 62 moves stage 20 in the X2' direction for the set period at the set first speed without any stop during the movement.

Figure 10:
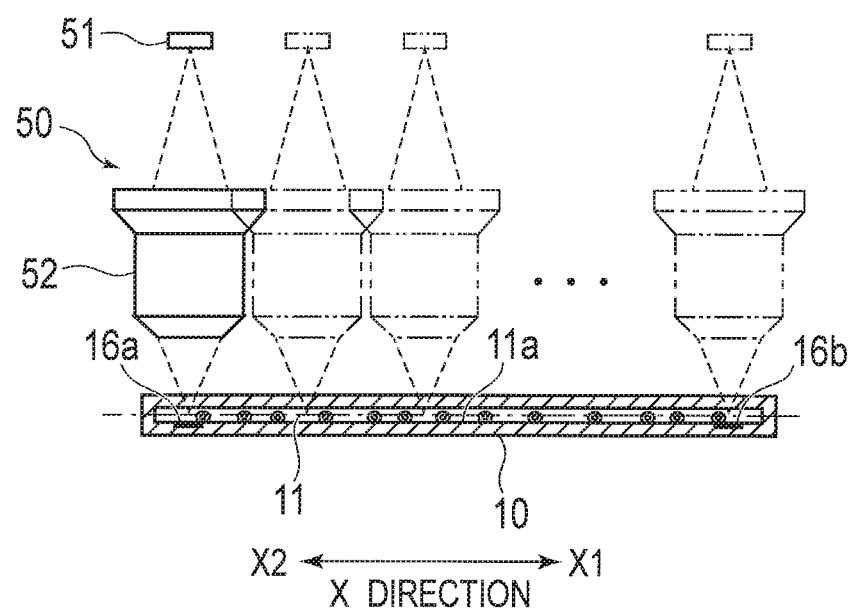
FIG. 10 is a diagram for illustrating a focus adjustment of the image capture unit in an image capture operation.

In the image capture step of FIG. 10, CPU 71 controls image capture unit 50 to execute image capture multiple times. As stage 20 moves, the visual field of objective lens 52 moves in the X1 direction from first reference mark 16*a* to second reference mark 16*b*. Image capture unit 50 captures images at multiple image capture positions in a region between first reference mark 16*a* and second reference mark 16*b*.

When stage 20 continues to move in the X2' direction at a set speed, image capture unit 50 continues to move in the Z2 direction at the first moving speed indicated in the first speed information. The X2' direction includes a component in the Z2 direction and a component in the X2 direction. The movement of stage 20 in the X2' direction means that stage 20 moves in the Z2 direction and the X2 direction. In other words, when stage 20 moves in the X2' direction, bottom surface 11*a* of inner space 11 of first specimen cell 10*a* moves in the Z2 direction. By the movement of objective lens 52 in the Z2 direction, the distance between bottom surface 11*a* and objective lens 52 is kept constant. Accordingly, objective lens 52 moves relative to first specimen cell 10*a* in parallel with bottom surface 11*a* of inner space 11. In other words, the position of objective lens 52 with respect to first specimen cell 10*a* and second specimen cell 10*b* moves in the X direction.

When objective lens 52 is at the position facing first reference mark 16*a*, the focus of objective lens 52 is on a position away from bottom surface 11*a* by the offset amount in the upward direction. For this reason, the focus of objective lens 52 relatively moves on a straight line extending in the X direction and being away from bottom surface 11*a* by the offset amount in the upward direction. Accordingly, when objective lens 52 and first specimen cell 10*a* moves relative to each other, the focus of objective lens 52 is positioned near bottom surface 11*a* of inner space 11 at each image capture position. As a result, a state where objective lens 52 is focused on a cell is maintained, and clear images of cells can be obtained stably. In addition, when stage 20 continues to move at the constant speed, light source 41 emits pulsed light at regular intervals. Hence, unblurred images can be obtained even without stopping stage 20 at every image capture.

In the image capture step, the focus is adjusted by moving objective lens 52 at the determined and constant moving speed, without detecting the in-focus state at every image capture position. Accordingly, the time of the image capture step can be shortened. In addition, the focus position does not affected by the concentration of the cells or the sizes of the cells in the urine specimen, and the same focus position can be employed at all the image capture positions. Since images are captured with stage 20 kept moving in the X2' direction, it is unnecessary to stop stage 20 at each image capture position for the image capture. Hence, it is possible to prevent vibration of cells in the urine specimen due to the stop of stage 20. Accordingly, it is unnecessary to wait until the vibration of the cells stops, and clear images of cells can be obtained stably.

After the set period has passed from the start of the movement of image capture unit 50 and stage 20, objective lens 52 is located at a position facing second reference mark 16*b* of first specimen cell 10*a*. In other words, second reference mark 16*b* is positioned on the optical axis of image capture unit 50. Here, image capture unit 50 and stage 20 stop, and the image capture step is completed.

Figure 8A:
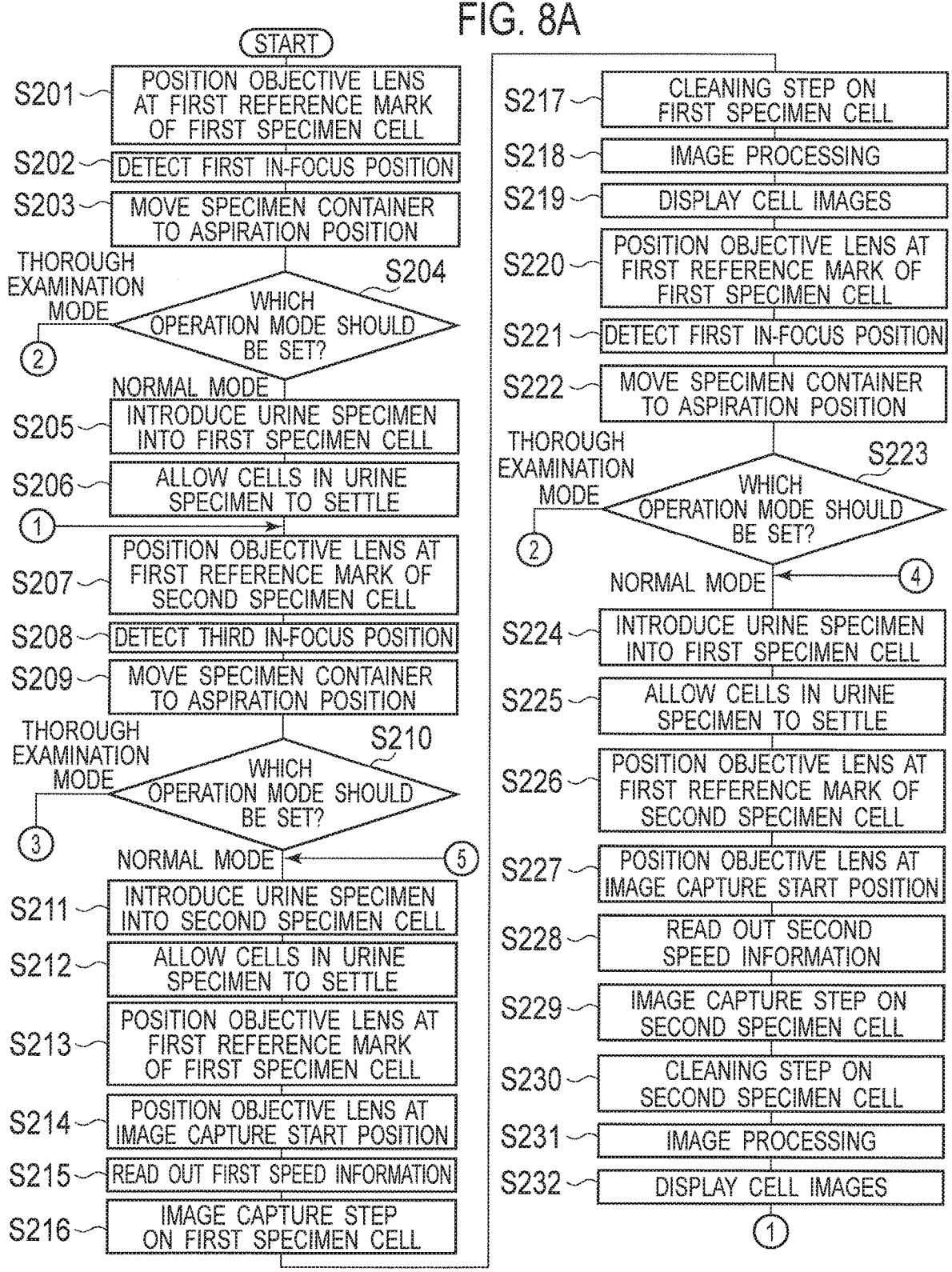
FIG. 8A is a flowchart illustrating a procedure of a urine specimen image capture process in a normal mode.

In Step S217 of FIG. 8A, CPU 71 controls specimen introduction unit 150 and drive unit 156 to move aspiration tube 151 to cleaning bath 154 and clean first specimen cell 10a and aspiration tube 151, which have been used for the image capture of the cells, with the buffer. Hereinafter, Step S217 is referred to as "cleaning step."

Images outputted from image capture element 51 as signals are inputted to controller 70, and stored in memory 72. In Step S218, CPU 71 executes image processing to cut out partial images of cells and other formed elements from the images obtained by image capture unit 50.

Figure 11:
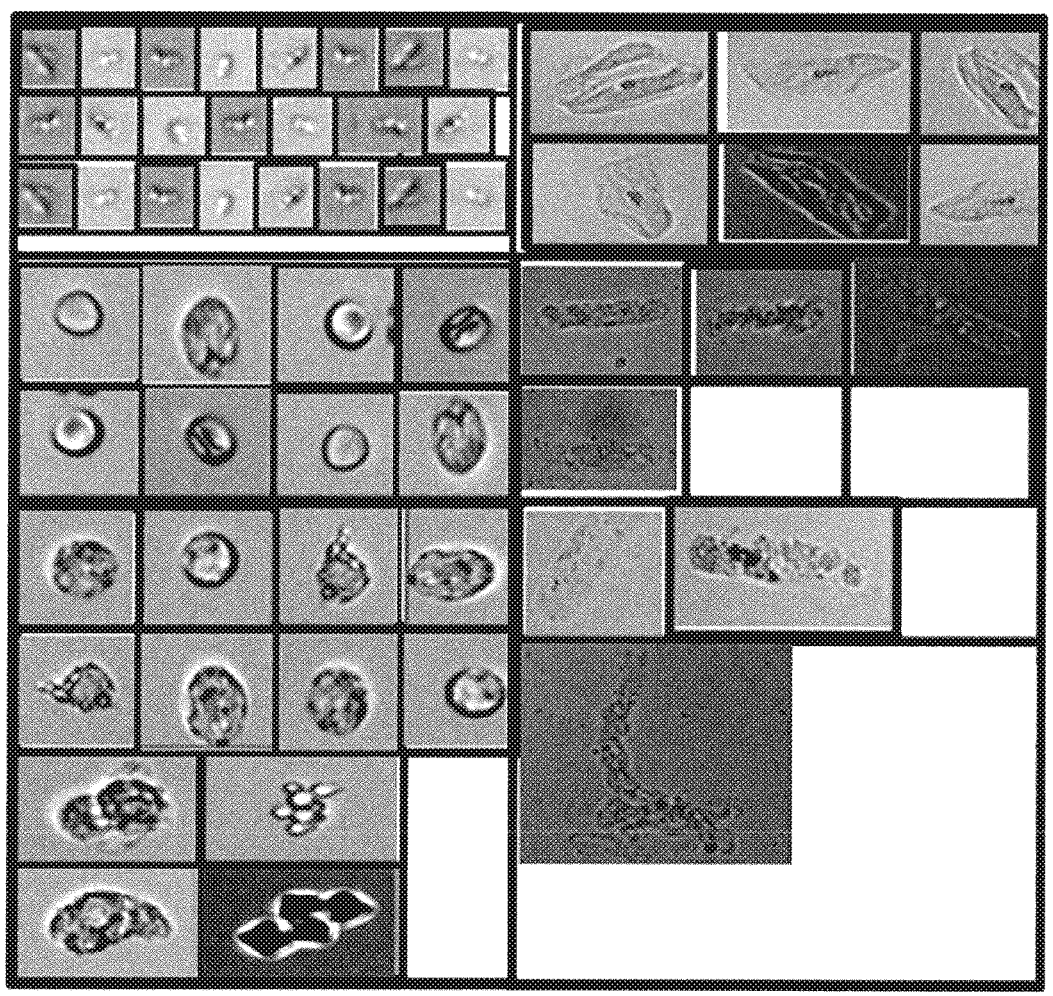
FIG. 11 illustrates an example of display of cell images.

In Step S219, CPU 71 displays the cut-out partial images on display unit 80. FIG. 11 illustrates an example of image display in the cell imaging apparatus. As illustrated in FIG. 11, display unit 80 displays multiple arranged images of cells and other formed elements contained in a single urine specimen.

In Step S220 of FIG. 8A, CPU 71 controls second drive unit 62 to move stage 20 in the X1' direction and position image capture unit 50 at first reference mark 16a of first specimen cell 10a.

In Step S221, CPU 71 executes the autofocus step on first specimen cell 10a. In other words, CPU 71 detects the first in-focus position, which is the in-focus position of objective lens 52 at first reference mark 16a of first specimen cell 10a. The process in Step S221 is the same as that in Step S202.

In Step S222, CPU 71 controls transport unit 170 to transport rack 161 and position specimen container 160 containing a next urine specimen to be subjected to the image capture to the aspiration position.

In Step S223, CPU 71 determines whether the urine specimen to be subjected to the image capture should be subjected to the image capture in the normal mode or in the thorough examination mode. The process in Step S223 is the same as that in Step S204.

When the urine specimen should be subjected to the image capture in the normal mode, CPU 71 proceeds to "normal mode" in Step S223, and executes Step S224. When the urine specimen should be subjected to image capture in the thorough examination mode, CPU 71 proceeds to "thorough examination mode" in Step S223, and executes Step S233.

In Step S224, CPU 71 executes the specimen introduction step on first specimen cell 10a. The process in Step S224 is the same as that in Step S205.

In Step S225, CPU 71 starts the settlement step on first specimen cell 10a. In other words, CPU 71 waits for a predetermined period, for example, for 100 seconds.

In Step S226, during the settlement step on first specimen cell 10a, CPU 71 controls second drive unit 62 to move stage 20 in the X2' direction and position image capture unit 50 at first reference mark 16a of second specimen cell 10b. The moving speed of stage 20 in Step S226 is the second speed as in the case of Step S201.

In Step S227, CPU 71 controls first drive unit 61 to position objective lens 52 at an image capture start position, which is a corrected position away from the third in-focus position by the predetermined offset amount in the upward direction.

In Step S228, CPU 71 reads out the second speed information for second specimen cell 10b from memory 72.

After completion of the settlement step on second specimen cell 10b, CPU 71 executes in Step S229 the image capture step of capturing images of cells in the urine specimen held in second specimen cell 10b at multiple image capture positions. In the image capture step on second specimen cell 10b, CPU 71 controls second drive unit 62 to move stage 20 at the first speed in the X2' direction, and controls first drive unit 61 to move image capture unit 50 at the second moving speed in the Z2 direction. As a result, first specimen cell 10a and second specimen cell 10b are moved in the X direction with respect to objective lens 52, and the visual field of objective lens 52 moves in the X1 direction in inner space 11 of second specimen cell 10b.

In each of the image capture steps on first specimen cell 10a and second specimen cell 10b, stage 20 moves in the X2' direction, which is one side of the X' direction, and objective lens 52 moves in the Z2 direction, which is one side of the Z direction. For example, as illustrated in FIG. 7, stage 20 moves to the lower left in FIG. 7, and objective lens 52 moves downward in FIG. 7. As a result, the moving direction of stage 20 and the moving direction of objective lens 52 are the same between the image capture steps on first specimen cell 10a and second specimen cell 10b. This facilitates the control of drive unit 60.

As shown in FIG. 8A, after completion of the image capture step, CPU 71 executes in Step S230 the cleaning step on second specimen cell 10b. In other words, CPU 71 controls specimen introduction unit 150 and drive unit 156 to move aspiration tube 151 to cleaning bath 154 and clean second specimen cell 10b and aspiration tube 151, which have been used for the image capture of the cells, with the buffer.

Images outputted from image capture element 51 as signals are inputted to controller 70, and stored in memory 72. In Step S231, CPU 71 executes image processing to cut out partial images of cells and other formed elements from the images obtained by image capture unit 50.

In Step S232, CPU 71 displays the cut-out partial images on display unit 80.

Next, CPU 71 proceeds to Step S207. After that, CPU 71 executes steps on second specimen cell 10b.

In the case of first specimen cell 10a, the autofocus operation is executed only for the detection of the first in-focus position at first reference mark 16a. In the case of second specimen cell 10b, the autofocus operation is executed only for the detection of the third in-focus position at first reference mark 16a. However, the following configuration may be employed. Specifically, pieces of information indicating the first and second in-focus positions detected in the moving speed determination operation are stored. For capturing images in first specimen cell 10a, the stored information indicating the first in-focus position is used to position objective lens 52 at the first in-focus position. Meanwhile, for capturing images in second specimen cell 10b, the stored information indicating the third in-focus position is used to position objective lens 52 at the third in-focus position. This eliminates the need for the execution of the autofocus operation of objective lens 52 to detect the first in-focus position and the third in-focus position in the urine specimen image capture process. Consequently, the image capture of urine specimens can be conducted in a much shorter time. Note, however, that when the first in-focus position and the third in-focus position determined in the moving speed determination operation are used, the focus of objective lens 52 may be shifted from bottom surface 11a of inner space 11 because of the temperature environment in the facility or the like, as described above. For this reason, it is preferable to detect the first in-focus position and the third in-focus position in the urine specimen image capture process from the viewpoint of obtaining clear in-focus images.

When multiple urine specimens are subjected to image capture successively, substantially no change in temperature in the image capture occurs among the successive urine specimens because of the short time intervals. For this reason, it is also possible to employ a configuration in which the first in-focus position and the third in-focus position are detected for every multiple urine specimens, for example, every five urine specimens instead of the configuration in which the first in-focus position and the third in-focus position are detected for every urine specimen. This makes it possible to reduce the number of times of the detection of the first in-focus position and the third in-focus position, while the state where the cells in each urine specimen are in focus is being maintained. As a result, the time can be saved.

In the urine specimen image capture process, the second in-focus position and the fourth in-focus position may be detected in addition to the first in-focus position and the third in-focus position. In this case, CPU 71 determines the moving speed of image capture unit 50 for each urine specimen. Accordingly, it is unnecessary to execute the moving speed determination operation during the initialization operation. This makes it possible to precisely adjust the focus of objective lens 52 in each image capture step.

The following configuration may be employed. Specifically, instead of the use of first reference mark 16a and second reference mark 16b, relative distances from multiple positions on bottom surface 11a of inner space 11 are detected by using an optical or ultrasonic distance sensor. Then, the coordinates of the multiple positions are determined on the basis of the detected relative positions. After that, the inclination of the X' direction from the horizontal direction is detected on the basis of the determined coordinates.

Next, operations of cell imaging apparatus 100 in the thorough examination mode are described.

The thorough examination mode is an operation mode in which a larger number of images of cells contained in a urine specimen to be subjected to thorough examination are captured and a larger number of cell images are obtained than in the normal mode to examine the urine specimen in details. For example, a specimen subjected to the thorough examination may be a urine specimen which is highly likely to contain urinary casts. Another specimen subjected to the thorough examination may be a urine specimen determined to be protein-positive by an analysis conducted with a urine qualitative analyzer in advance. Another specimen subjected to the thorough examination may be a urine specimen in which any of urinary casts and epithelial cells other than squamous epithelial cells is detected in an analysis of the urine specimen conducted with a urine formed element analyzer in advance.

In the thorough examination mode, aliquots of a single urine specimen taken from a single subject are introduced into first specimen cell 10a and second specimen cell 10b, and images of cells are captured in each of first specimen cell 10a and second specimen cell 10b. For this reason, a larger number of images of cells are obtained in the thorough examination mode than in the normal mode.

Figure 8B:
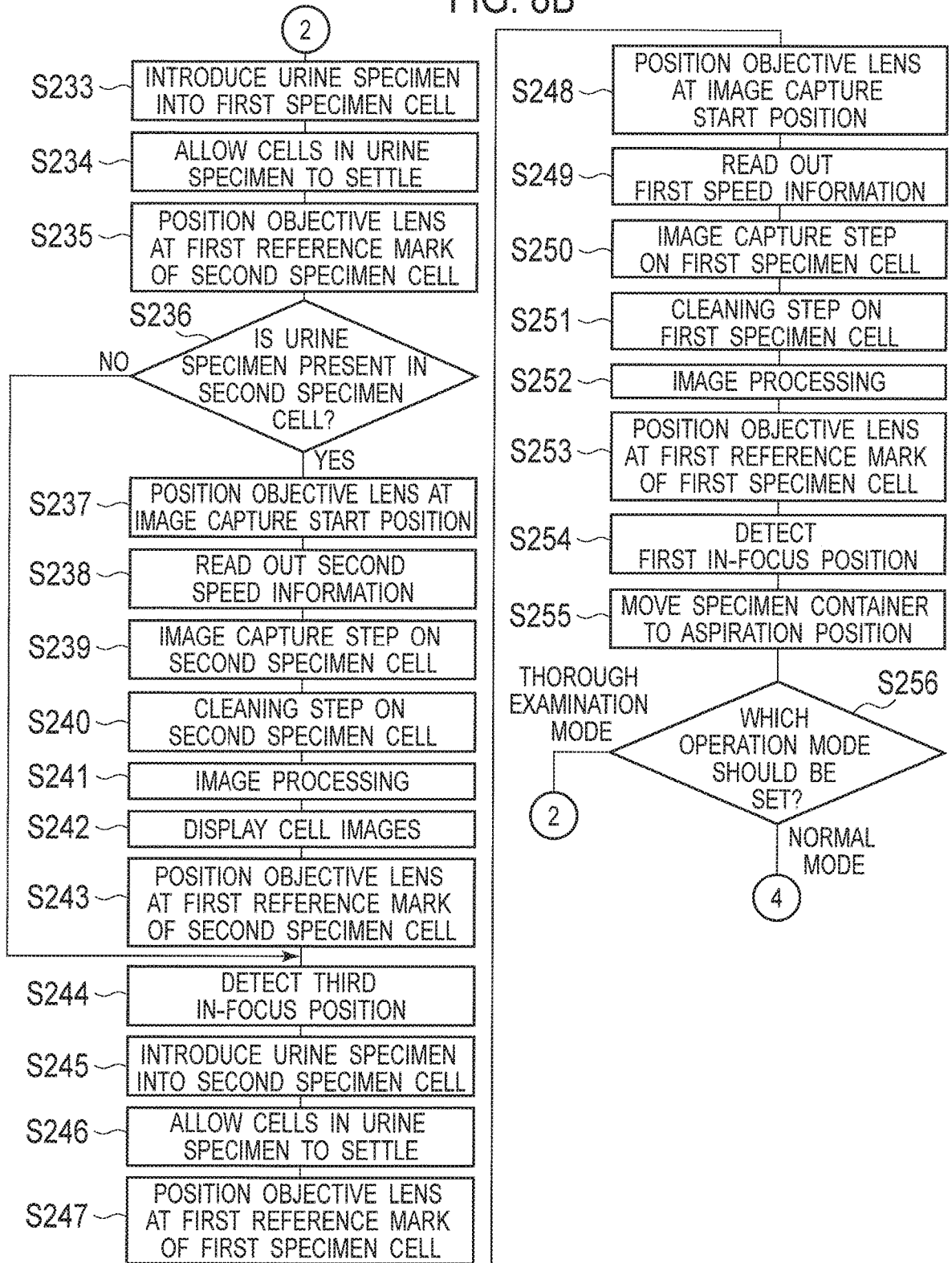
FIG. 8B is a flowchart illustrating a procedure of a urine specimen image capture process in a thorough examination mode.

As shown in FIG. 8B, when CPU 71 proceeds to the "thorough examination mode" in Step S204 or S223, CPU 71 executes the processes in Step S233 and later. In Step S233 and later, aliquots of a urine specimen to be subjected to the thorough examination are introduced into first specimen cell 10a and second specimen cell 10b. After that, the image capture step is executed on first specimen cell 10a, and then the image capture step is executed on second specimen cell 10b.

In Step S233, CPU 71 executes the specimen introduction step on first specimen cell 10a. The process in Step S233 is the same as that in Step S205. Thus, the urine specimen to be subjected to the thorough examination is introduced into inner space 11 of first specimen cell 10a.

In Step S234, CPU 71 starts the settlement step on first specimen cell 10a. In other words, CPU 71 waits for a predetermined period, for example, for 100 seconds.

In Step S235, during the settlement step on first specimen cell 10a, CPU 71 controls second drive unit 62 to move stage 20 in the X2' direction and position image capture unit 50 at first reference mark 16a of second specimen cell 10b. The moving speed of stage 20 in Step S234 is the second speed as in the case of Step S201.

In Step S236, CPU 71 determines whether or not a urine specimen has been already introduced in inner space 11 of second specimen cell 10b. The fact that a specimen has been already introduced in second specimen cell 10b means that second specimen cell 10b is being subjected to the settlement step. When a urine specimen has been introduced in inner space 11 of second specimen cell 10b, CPU 71 proceeds to YES in Step S236, and executes Step S237. When no urine specimen has been introduced yet in inner space 11 of second specimen cell 10b, CPU 71 proceeds to NO in Step S236, and executes Step S244.

In the processes in Steps S237 to S242, the image capture step, the cleaning step, and the cell image display are executed on second specimen cell 10b. The processes in Steps S237 to S242 are the same as those in Steps S227 to S232. After Step S242, CPU 71 executes Step S243.

In Step S243, CPU 71 controls second drive unit 62 to move stage 20 in the X1' direction and position image capture unit 50 at first reference mark 16a of second specimen cell 10b.

In Step S244, the autofocus step is executed on second specimen cell 10b. In other words, CPU 71 detects the third in-focus position, which is the in-focus position of objective lens 52 at first reference mark 16a of second specimen cell 10b. The process in Step S244 is the same as that in Step S202.

In Step S245, CPU 71 controls drive unit 156 and specimen introduction unit 150 to insert aspiration tube 151 into specimen container 160, aspirate a predetermined amount of a urine specimen from specimen container 160, and introduce the urine specimen to be subjected to the thorough examination into inner space 11 of second specimen cell 10b. In Step S245, the urine specimen introduced into second specimen cell 10b is the same as the urine specimen already introduced in inner space 11 of first specimen cell 10a.

In Step S246, CPU 71 starts the settlement step on second specimen cell 10b. In other words, CPU 71 waits for a predetermined period, for example, for 100 seconds.

In Step S247, during the settlement step on second specimen cell 10b, CPU 71 controls second drive unit 62 to move stage 20 in the X1' direction and position image capture unit 50 at first reference mark 16a of first specimen cell 10a. The moving speed of stage 20 in Step S247 is the second speed as in the case of Step S201.

In Step S248, CPU 71 controls first drive unit 61 to position objective lens 52 at an image capture start position, which is a position corrected from the first in-focus position by a predetermined offset amount in the upward direction.

In Step S249, CPU 71 reads out first speed information for first specimen cell 10a from memory 72.

After completion of the settlement step on first specimen cell 10a, CPU 71 executes in Step S250 the image capture step on first specimen cell 10a. The process in Step S250 is the same as that in Step S216.

After completion of the image capture step, CPU 71 executes in Step S251 the cleaning step on first specimen cell 10*a*. In other words, CPU 71 controls specimen introduction unit 150 and drive unit 156 to move aspiration tube 151 to cleaning bath 154 and clean first specimen cell 10*a* and aspiration tube 151, which have been used for the image capture of the cells, with the buffer.

Images outputted from image capture element 51 as signals are inputted to controller 70, and stored in memory 72. In Step S252, CPU 71 executes image processing to cut out partial images of cells and other formed elements from the images obtained by image capture unit 50.

In Step S253, CPU 71 controls second drive unit 62 to move stage 20 in the X1' direction and position image capture unit 50 at first reference mark 16*a* of first specimen cell 10*a*.

In Step S254, CPU 71 executes the autofocus step on first specimen cell 10*a*. In other words, CPU 71 detects the first in-focus position, which is the in-focus position of objective lens 52 at first reference mark 16*a* of first specimen cell 10*a*. The process in Step S254 is the same as that in Step S202.

In Step S255, CPU 71 controls transport unit 170 to transport rack 161 and position specimen container 160 containing a next urine specimen to be subjected to the image capture at the aspiration position.

In Step S256, CPU 71 determines whether the urine specimen to be subjected to the image capture should be subjected to the image capture in the normal mode or in the thorough examination mode. The process in Step S256 is the same as that in Step S204.

When the urine specimen should be subjected to the image capture in the normal mode, CPU 71 proceeds to "normal mode" in Step S256, and executes Step S224.

See FIG. 8A. In Step S224, CPU 71 executes the specimen introduction step on first specimen cell 10*a* to introduce the next urine specimen into inner space 11 of first specimen cell 10*a*.

In Step S225, CPU 71 starts the settlement step on first specimen cell 10*a*. In other words, CPU 71 waits for a predetermined period, for example, for 100 seconds.

In Step S226, during the settlement step on first specimen cell 10*a*, CPU 71 controls second drive unit 62 to move stage 20 in the X2' direction and position image capture unit 50 at first reference mark 16*a* of second specimen cell 10*b*.

In Step S227, CPU 71 controls first drive unit 61 to position objective lens 52 at an image capture start position, which is a corrected position away from the third in-focus position by the predetermined offset amount in the upward direction.

In Step S228, CPU 71 reads out the second speed information for second specimen cell 10*b* from memory 72.

After completion of the settlement step on second specimen cell 10*b*, CPU 71 executes in Step S229 the image capture step on second specimen cell 10*b*. The urine specimen introduced in inner space 11 of second specimen cell 10*b* is a urine specimen to be subjected to the thorough examination.

After completion of the image capture step, CPU 71 executes in Step S230 the cleaning step on second specimen cell 10*b*.

Images outputted from image capture element 51 as signals are inputted to controller 70, and stored in memory 72. In Step S231, CPU 71 executes image processing to cut out partial images of cells and other formed elements from the images obtained by image capture unit 50.

In Step S232, CPU 71 displays the cut-out partial images on display unit 80. The partial images displayed here are those of cells contained in the urine specimen subjected to the thorough examination. In the thorough examination mode, CPU 71 displays on a single screen multiple images of cells and formed elements obtained in the image capture steps on first specimen cell 10*a* and second specimen cell 10*b*. The number of images displayed per single urine specimen subjected to the thorough examination is approximately twice the number of images displayed per single urine specimen in the normal mode.

For example, in the thorough examination mode, it is possible to execute the image capture step three times on a single urine specimen by introducing the urine specimen subjected to the image capture twice into first specimen cell 10*a* and once into second specimen cell 10*b* and capturing images of cells. It is also possible to execute the image capture step on a single urine specimen more times by introducing the urine specimen to be subjected to the image capture multiple times into each of first specimen cell 10*a* and second specimen cell 10*b* and capturing images of cells.

Next, CPU 71 proceeds to Step S207. After that, CPU 71 executes steps on second specimen cell 10*b*.

On the other hand, when the urine specimen is determined to be subjected to the thorough examination in Step S256, CPU 71 proceeds to "thorough examination mode", and executes Step S233.

See FIG. 8B. In this case, in the processes in Steps S237 to S242, the image capture step, the cleaning step, and the cell image display are executed on the urine specimen subjected to the thorough examination already introduced in the inner space of second specimen cell 10*b*. Images displayed in Step S242 are those of cells contained in the urine specimen subjected to the thorough examination, and include both images obtained by the image capture in first specimen cell 10*a* and images obtained by the image capture in second specimen cell 10*b*.

See again FIG. 8A. When CPU 71 proceeds to the "thorough examination mode" in Step S210, CPU 71 executes the processes in Step S257 and later.

Figure 8C:
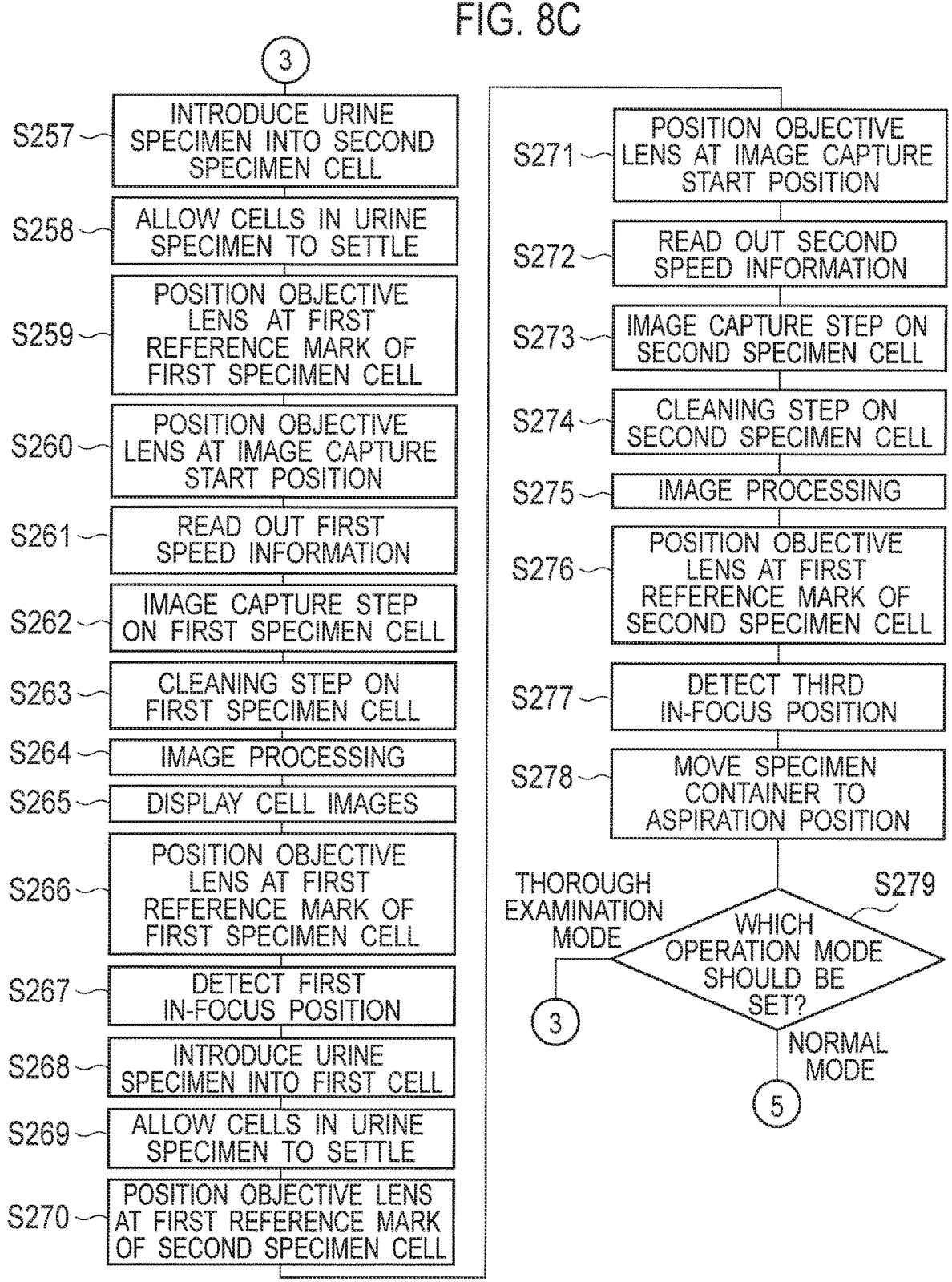
FIG. 8C is a flowchart illustrating a procedure of urine specimen image capture process in the thorough examination mode.

See FIG. 8C. In Step S257 and later, a urine specimen to be subjected to the thorough examination is introduced into each of second specimen cell 10*b* and first specimen cell 10*a*, and the image capture step is executed on second specimen cell 10*b*. After that, the image capture step is executed on first specimen cell 10*a*. In other words, the order of the processes on first specimen cell 10*a* and on second specimen cell 10*b* in Steps S233 to S256 is reversed in Steps S257 to 279. Since the details of the processes are the same, descriptions of the processes are omitted. Note that, after the cell imaging apparatus 100 completes the initialization operation and is placed in the standby state, the urine specimen is introduced first into first specimen cell 10*a* in this embodiment. Hence, when a urine specimen to be subjected to the thorough examination is introduced in second specimen cell 10*b*, a urine specimen has always been introduced in inner space 11 of first specimen cell 10*a*. Accordingly, the process of determining whether or not a urine specimen has been already introduced in inner space 11 of first specimen cell 10*a*, i.e., a process corresponding to Step S236 described above is not executed.

Figure 12:
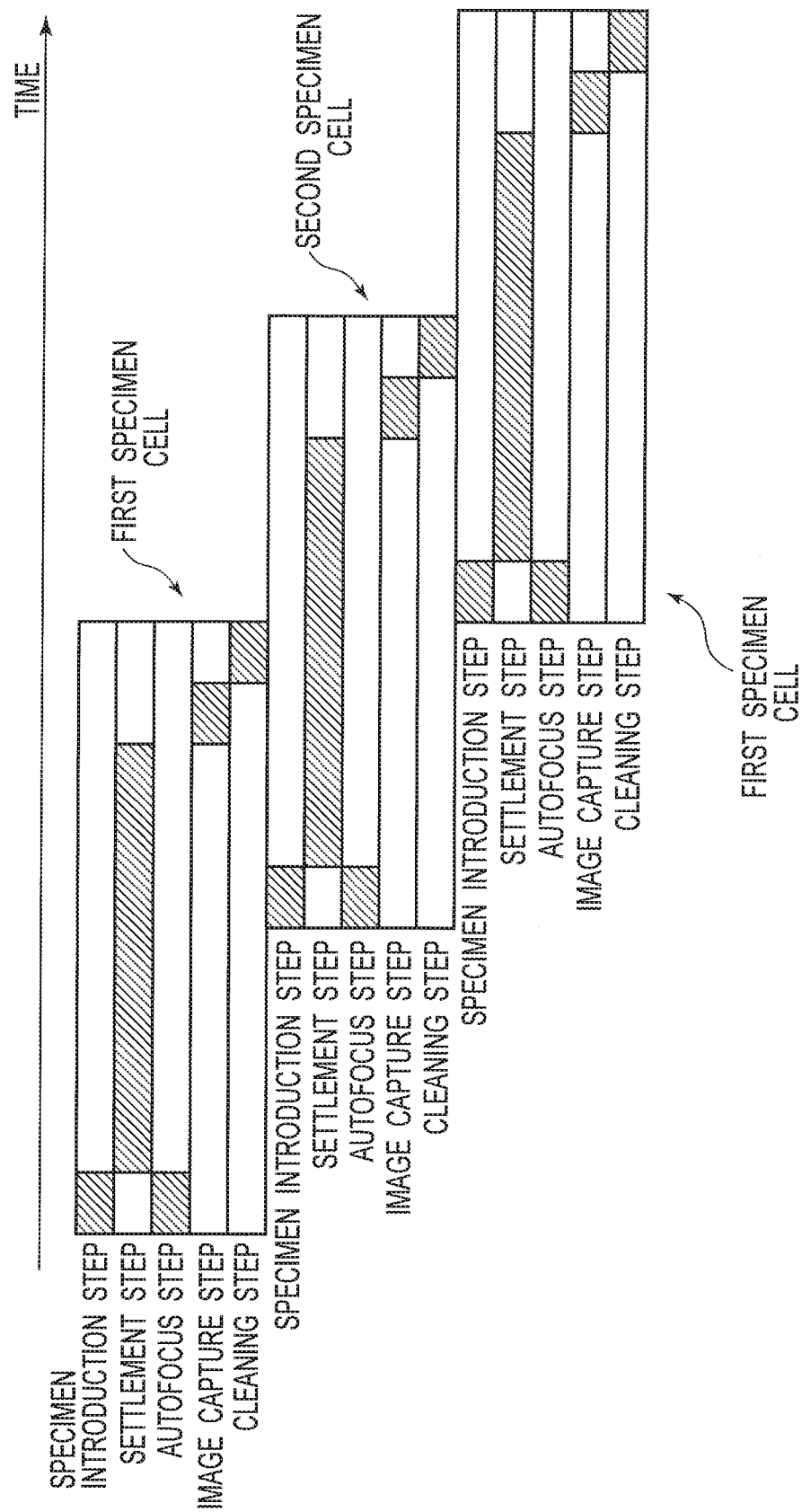
FIG. 12 is a timing chart illustrating operations of the cell imaging apparatus.

As described above, cell imaging apparatus 100 efficiently captures images of cells by executing the steps on first specimen cell 10*a* and the steps on second specimen cell 10*b* in an overlapping manner. This point will be described in detail with reference to FIG. 12.

When the urine specimen image capture process is started, CPU 71 simultaneously executes the specimen introduction step and the autofocus step on first specimen cell 10*a*. Here, image capture unit 50 is disposed to face first specimen cell 10a for the autofocus step. The specimen introduction step and the autofocus step may be executed in different periods.

After completion of the specimen introduction step and the autofocus step, CPU 71 starts the settlement step on first specimen cell 10a. While executing the settlement step on first specimen cell 10a, CPU 71 executes the specimen introduction step and the autofocus step on second specimen cell 10b. Here, in the normal mode, the urine specimen introduced into first specimen cell 10a and the urine specimen introduced into second specimen cell 10b are different urine specimens taken from different subjects. In the thorough examination mode, the urine specimen introduced into first specimen cell 10a and the urine specimen introduced into second specimen cell 10b are the same urine specimen taken from a single subject.

To execute the autofocus step on second specimen cell 10b, image capture unit 50 has to be disposed to face second specimen cell 10b. Accordingly, CPU 71 causes second drive unit 62 to move stage 20 in the X2' direction, position image capture unit 50 at a position facing second specimen cell 10b, and then execute the autofocus step during the settlement step on first specimen cell 10a.

CPU 71 starts the settlement step on second specimen cell 10b. A final stage of the settlement step on first specimen cell 10a overlaps with an initial stage of the settlement step on second specimen cell 10b.

After completion of the settlement step on first specimen cell 10a, CPU 71 executes the image capture step on first specimen cell 10a. Before the image capture step is started on first specimen cell 10a, image capture unit 50 faces second specimen cell 10b. Hence, to execute the image capture step on first specimen cell 10a, the image capture unit 50 has to be disposed to face first specimen cell 10a. Accordingly, CPU 71 causes second drive unit 62 to move stage 20 in the X1' direction, position image capture unit 50 to a position facing first specimen cell 10a, and then execute the image capture step during the settlement step on second specimen cell 10b.

After completion of the image capture step, CPU 71 executes the cleaning step on first specimen cell 10a. Thus, a series of steps (hereinafter, referred to as "image capture sequence") on first specimen cell 10a is completed.

After completion of the image capture sequence on first specimen cell 10a, CPU 71 starts another image capture sequence on first specimen cell 10a. At the start of the image capture sequence on first specimen cell 10a, the settlement step on second specimen cell 10b is being executed. In other words, while executing the settlement step on second specimen cell 10b, CPU 71 executes the specimen introduction step and the autofocus step on first specimen cell 10a. Here, in the normal mode, a urine specimen taken from a subject different from the subject from which the urine specimen introduced in second specimen cell 10b is taken is introduced into first specimen cell 10b. In the thorough examination mode, the same urine specimen taken from the same subject from which the urine specimen introduced in second specimen cell 10b is taken is introduced into first specimen cell 10b.

At the start of the image capture sequence on first specimen cell 10a, image capture unit 50 faces first specimen cell 10a. Accordingly, CPU 71 executes the specimen introduction step and the autofocus step on first specimen cell 10a, without switching the position of image capture unit 50 between first specimen cell 10a and second specimen cell 10b.

After completion of the specimen introduction step and the autofocus step, CPU 71 starts the settlement step on first specimen cell 10a. A final stage of the settlement step on second specimen cell 10b overlaps with an initial stage of the settlement step on first specimen cell 10a.

After completion of the settlement step on second specimen cell 10b, CPU 71 executes the image capture step on second specimen cell 10b. Before the image capture step on second specimen cell 10b is started, image capture unit 50 faces first specimen cell 10a. Hence, to execute the image capture step on second specimen cell 10b, image capture unit 50 has to be disposed to face second specimen cell 10b. Accordingly, CPU 71 causes second drive unit 62 to move stage 20 in the X2' direction, position image capture unit 50 to a position facing second specimen cell 10b, and then execute the image capture step during the settlement step on first specimen cell 10a.

After completion of the image capture step, CPU 71 executes the cleaning step on second specimen cell 10b.

After that, CPU 71 executes the specimen introduction step, the autofocus step, the settlement step, the image capture step, and the cleaning step on each of first specimen cell 10a and second specimen cell 10b in the same manner.

As described above, the image capture step on first specimen cell 10a and the settlement step on second specimen cell 10b are executed simultaneously, and the image capture step on second specimen cell 10b and the settlement step on first specimen cell 10a are executed simultaneously. Accordingly, images of cells can be captured efficiently, while single image capture unit 50 is shared by first specimen cell 10a and second specimen cell 10b.

The specimen introduction step on first specimen cell 10a and the settlement step on second specimen cell 10b are executed simultaneously, and the specimen introduction step on second specimen cell 10b and the settlement step on first specimen cell 10a are executed simultaneously. Accordingly, by utilizing the time of the cell settlement step on one specimen cell 10, a urine specimen can be introduced in the other specimen cell 10, while single aspiration tube 151 is shared by first specimen cell 10a and second specimen cell 10b. Thus, images of cells can be captured efficiently.

The image capture step on one specimen cell 10 and the specimen introduction step or the cleaning step on the other specimen cell 10 may be executed simultaneously. Also with this configuration, the urine specimen image capture processes on first specimen cell 10a and second specimen cell 10b can be carried out simultaneously. Hence, images of cells can be captured efficiently, while single image capture unit 50 is shared by first specimen cell 10a and second specimen cell 10b.

As described above, inner spaces 11 of first specimen cell 10a and second specimen cell 10b extend in the X direction. Hence, by moving first specimen cell 10a and second specimen cell 10b in the X' direction, the visual field of objective lens 52 is moved in the X direction. Hence, images of cells can be captured in each of first specimen cell 10a and second specimen cell 10b. First specimen cell 10a and second specimen cell 10b are aligned in the X direction in a row. Hence, by moving first specimen cell 10a and second specimen cell 10b in the X' direction, objective lens 52 can be moved between first specimen cell 10a and second specimen cell 10b. This makes it possible to rapidly capture images of cells held in first specimen cell 10a and second specimen cell 10b and rapidly switch specimen cell 10 subjected to the image capture, making it possible to improve the efficiency of image capture of multiple specimens.

Suppose a case where the sample processing system disclosed in Japanese Patent Application Publication No. 2010-169484 completes image capture of one specimen and starts image capture of the next specimen. In such a case, it is necessary to detach the microscope slide whose image capture is completed from the XY stage and then set a microscope slide smeared with the next specimen on the XY stage. For this reason, capturing images of multiple specimens successively takes a long time, and this sample processing system is incapable of efficiently capturing images of multiple specimens.

According to this embodiment, it is possible to improve the efficiency of image capture of multiple specimens in comparison with a conventional case.

The invention includes other embodiments in addition to the above-described embodiments without departing from the spirit of the invention. The embodiments are to be considered in all respects as illustrative, and not restrictive. The scope of the invention is indicated by the appended claims rather than by the foregoing description. Hence, all configurations including the meaning and range within equivalent arrangements of the claims are intended to be embraced in the invention.

The invention claimed is:

1. A cell imaging apparatus that captures images of cells contained in a liquid specimen, comprising:
    an image capture unit including an objective lens;
    specimen cells each including an inner space which is capable of holding a liquid specimen and which is elongated in one direction, the specimen cells arranged such that the inner spaces are aligned in a row in a longitudinal direction of the inner spaces;
    a drive unit that moves at least one of: a) one or more specimen cells; and b) the objective lens; and
    a controller that controls the drive unit to move at least one of: a) one or more specimen cells; and b) the objective lens in the longitudinal direction and controls the image capture unit to capture images of cells contained in a liquid specimen held in the inner space of each of the specimen cells at multiple image capture positions, wherein
    each of the specimen cells comprises:
        an inlet port extending from one end of the inner space in the longitudinal direction and through which a liquid specimen is introduced into the inner space of each of the specimen cells; and
        an outlet port extending from another end of the inner space in the longitudinal direction and through which a liquid specimen flows out from the inner space of each of the specimen cells.

2. The cell imaging apparatus according to claim 1, wherein
    the specimen cells are arranged such that the longitudinal direction intersects with a vertical direction.

3. The cell imaging apparatus according to claim 1, further comprising a stage to which the specimen cells are attached, wherein
    the drive unit moves the specimen cells by moving the stage.

4. The cell imaging apparatus according to claim 3, wherein
    the specimen cells are aligned on the stage in one horizontal direction.

5. The cell imaging apparatus according to claim 4, wherein
    the objective lens is arranged with an optical axis direction of the objective lens intersecting with the longitudinal direction,
    the drive unit moves the objective lens in the optical axis direction and moves the stage in an inclined direction inclined from the longitudinal direction to the optical axis direction, and
    the controller adjusts a focus of the objective lens at each of the image capture positions by controlling the drive unit to move the stage in the inclined direction and simultaneously move the objective lens in the optical axis direction according to a moving amount of the stage.

6. The cell imaging apparatus according to claim 5, wherein
    the drive unit includes a restriction unit that restricts a moving direction of the stage to the inclined direction.

7. The cell imaging apparatus according to claim 5, wherein
    the controller adjusts the focus of the objective lens at each of the image capture positions by controlling the drive unit to move the stage to one side of the inclined direction and simultaneously move the objective lens to one side of the optical axis direction.

8. The cell imaging apparatus according to claim 3, wherein
    the specimen cells are aligned on the stage in an inclined direction inclined from one horizontal direction to a vertical direction,
    the objective lens is arranged with an optical axis direction of the objective lens being equal to the vertical direction,
    the drive unit moves the objective lens in the optical axis direction and move the stage in the one horizontal direction,
    the controller adjusts a focus of the objective lens at each of the image capture positions by controlling the drive unit to move the stage in the one horizontal direction and to move the objective lens in the optical axis direction according to a moving amount of the stage.

9. The cell imaging apparatus according to claim 1, wherein
    the specimen cells include a first specimen cell and a second specimen cell, and
    in capturing images of cells contained in a liquid specimen held in the inner space of the first specimen cell, the controller controls the drive unit to move at least one of: a) one or more specimen cells; and b) the objective lens at a first speed, and
    in switching a specimen cell subjected to the image capture from the first specimen cell to the second specimen cell, the controller controls the drive unit to move at least one of: a) one or more specimen cells; and b) the objective lens at a second speed which is higher than the first speed.

10. The cell imaging apparatus according to claim 1, wherein
    the specimen cells include a first specimen cell and a second specimen cell, and
    the controller executes at least one of: introducing a second liquid specimen into the inner space of the second specimen cell; settling cells contained in the second liquid specimen held in the inner space of the second specimen cell after the introduction of the second liquid specimen; and cleaning the inner space of the second specimen cell, during execution of image capture of cells contained in a first liquid specimen held in the inner space of the first specimen cell.

11. The cell imaging apparatus according to claim 1, further comprising an aspiration unit that aspirates a liquid specimen, wherein
the specimen cells include a first specimen cell and a second specimen cell, and
the controller controls the aspiration unit to aspirate a second liquid specimen to be introduced into the inner space of the second specimen cell during a period in which cells in a first liquid specimen aspirated by the aspiration unit and introduced in the inner space of the first specimen cell are allowed to settle.

12. The cell imaging apparatus according to claim 11, wherein
the controller controls the drive unit and the image capture unit to execute image capture of cells contained in the first liquid specimen held in the inner space of the first specimen cell, during a period in which the cells in the second liquid specimen held in the inner space of the second specimen cell are allowed to settle.

13. The cell imaging apparatus according to claim 1, wherein
each of the specimen cells includes a reference mark used to adjust a focus of the objective lens, and
the reference marks are aligned in the longitudinal direction.

14. The cell imaging apparatus according to claim 1, wherein
each of the specimen cells is shaped like a flat cuboid extending in the longitudinal direction.

15. The cell imaging apparatus according to claim 1, further comprising:
an aspiration unit that aspirates a liquid specimen; and
a specimen introduction unit that introduces a liquid specimen aspirated by the aspiration unit into one of the specimen cells, wherein
the specimen cells include a first specimen cell and a second specimen cell, and
in a first mode, the controller controls the specimen introduction unit to introduce a liquid specimen obtained from a first subject and aspirated by the aspiration unit into the first specimen cell and introduce a liquid specimen obtained from a second subject different from the first subject and aspirated by the aspiration unit into the second specimen cell, whereas
in a second mode, the controller controls the specimen introduction unit to introduce an aliquot of a liquid specimen obtained from a subject and aspirated by the aspiration unit into the first specimen cell and introduce another aliquot of the liquid specimen obtained from the subject and aspirated by the aspiration unit into the second specimen cell.

16. The cell imaging apparatus according to claim 1, wherein
the liquid specimen is a urine specimen.

17. A cell imaging method using a first specimen cell and a second specimen cell each including an inner space which is capable of holding a liquid specimen and is elongated in one direction, the first and the second specimen cells arranged such that the inner spaces are aligned in a row in a longitudinal direction of the inner spaces, the method comprising:
introducing a first liquid specimen containing cells into the inner space of the first specimen cell;
introducing a second liquid specimen containing cells into the inner space of the second specimen cell;
capturing images of cells contained in the first liquid specimen held in the inner space of the first specimen cell at multiple image capture positions by moving at least one of: a) the first and second specimen cells; and b) an objective lens in the longitudinal direction; and
capturing images of cells contained in the second liquid specimen held in the inner space of the second specimen cell at multiple image capture positions by moving at least one of: a) the first and second specimen cells; and b) the objective lens in the longitudinal direction, wherein
each of the first specimen cell and the second specimen cell comprises:
an inlet port extending from one end of the inner space in the longitudinal direction and through which the first liquid specimen and the second liquid specimen are introduced into the inner space of the first specimen cell and the inner space of the second specimen cell, respectively; and
an outlet port extending from another end of the inner space in the longitudinal direction and through which the first liquid specimen and the second liquid specimen flow out from the inner space of the first specimen cell and the inner space of the second specimen cell, respectively.

18. The cell imaging method according to claim 17, wherein
during the capturing of the images of the cells contained in the first liquid specimen held in the inner space of the first specimen cell, the method involves executing at least one of: introducing the second liquid specimen into the inner space of the second specimen cell; settling the cells contained in the second liquid specimen held in the inner space of the second specimen cell after the introduction of the second liquid specimen; and cleaning the inner space of the second specimen cell.

19. The cell imaging method according to claim 17, wherein
during a period in which the cells in the first liquid specimen introduced in the inner space of the first specimen cell are allowed to settle, the second liquid specimen is introduced into the inner space of the second specimen cell.

20. A cell imaging method, comprising:
introducing a first liquid specimen containing cells into an inner space of a first specimen cell;
introducing a second liquid specimen containing cells into an inner space of a second specimen cell during a period in which the cells in the first liquid specimen are allowed to settle in the first specimen cell;
capturing images of the cells contained in the first liquid specimen in the first specimen cell during a period in which the cells in the second liquid specimen are allowed to settle in the second specimen cell;
after completion of the capturing of the images of the cells contained in the first liquid specimen, discharging the first liquid specimen from the first specimen cell and introducing a third liquid specimen containing cells into the first specimen cell; and
during a period in which the cells in the third liquid specimen are allowed to settle in the first specimen cell, capturing images of the cells contained in the second liquid specimen in the second specimen cell, wherein
each of the first specimen cell and the second specimen cell comprises:

an inlet port extending from one end of the inner space in a longitudinal direction of the inner space and through which the first liquid specimen and the second liquid specimen are introduced into the inner space of the first specimen cell and the inner space of the second specimen cell, respectively; and an outlet port extending from another end of the inner space in the longitudinal direction of the inner space and through which the first liquid specimen and the second liquid specimen flow out from the inner space of the first specimen cell and the inner space of the second specimen cell, respectively.

* * * * *